US012678558B2

(12) United States Patent
Jubic et al.

(10) Patent No.: US 12,678,558 B2
(45) Date of Patent: Jul. 14, 2026

(54) SYSTEM AND METHOD UTILIZING AN INTEGRATED CAMERA WITH A FLUID INJECTOR

(71) Applicant: BAYER HEALTHCARE LLC, Whippany, NJ (US)

(72) Inventors: Christopher Jubic, Valencia, PA (US); Daniel Manzo, Succasunna, NJ (US); Michael Haegg, McKees Rocks, PA (US); Nicholas Doolittle, Mars, PA (US); Joanne Hoener, New Kensington, PA (US); Linda Van Roosmalen, Gibsonia, PA (US); Nolan Zinn, McMurray, PA (US); David Griffiths, Pittsburgh, PA (US); Arthur Uber, III, Pittsburgh, PA (US); Ling Yu Hung, Pittsburgh, PA (US); Edward Prem, Allison Park, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 400 days.

(21) Appl. No.: 17/756,339

(22) PCT Filed: Nov. 23, 2020

(86) PCT No.: PCT/US2020/061733
§ 371 (c)(1),
(2) Date: May 23, 2022

(87) PCT Pub. No.: WO2021/108286
PCT Pub. Date: Jun. 3, 2021

(65) Prior Publication Data
US 2023/0173172 A1 Jun. 8, 2023

Related U.S. Application Data

(60) Provisional application No. 62/939,878, filed on Nov. 25, 2019.

(51) Int. Cl.
*A61M 5/145* (2006.01)
*A61M 5/42* (2006.01)

(52) U.S. Cl.
CPC ........ *A61M 5/14566* (2013.01); *A61M 5/427* (2013.01); *A61M 2205/6018* (2013.01)

(58) Field of Classification Search
CPC .............. A61M 5/14566; A61M 5/427; A61M 2205/6018; A61M 2205/6009;
(Continued)

(56) References Cited

U.S. PATENT DOCUMENTS

| 7,553,294 B2 | 6/2009 | Lazzaro et al. |
| 7,563,249 B2 | 7/2009 | Schriver et al. |

(Continued)

FOREIGN PATENT DOCUMENTS

| CN | 105993038 A | 10/2016 |
| CN | 206833462 U | 1/2018 |

(Continued)

OTHER PUBLICATIONS

"International Preliminary Report on Patentability from PCT Application No. PCT/US2020061733", Jun. 9, 2022.
(Continued)

*Primary Examiner* — Akwasi M Sarpong
*Assistant Examiner* — Michael L Burleson
(74) *Attorney, Agent, or Firm* — James R. Stevenson; Joseph L. Kent; Christopher P. Sherwin

(57) ABSTRACT

A fluid injector system configured for use in administering at least one fluid to a patient, the fluid injector system including at least one image capture device configured for capturing image data in an environment surrounding the fluid injector system; and a control device comprising at least one processor programmed or configured to receive, with the at least one processor, the image data captured by
(Continued)

the at least one image capture device; determine, with the at least one processor, whether the received image data comprises at least one predetermined characteristic; and perform, with the at least one processor, at least one action in response to determining whether the received image data comprises at least one predetermined characteristic.

20 Claims, 12 Drawing Sheets

(58) Field of Classification Search
CPC .. A61M 2205/6036; A61M 2205/6063; A61M 2205/6072; A61M 2205/6081; A61M 2205/609; A61M 5/1408; G05B 2219/35444
See application file for complete search history.

(56) References Cited

U.S. PATENT DOCUMENTS

| | | | |
|---|---|---|---|
| 8,452,380 B2 | 5/2013 | Williams et al. | |
| 8,945,051 B2 | 2/2015 | Schriver et al. | |
| 9,173,995 B1 | 11/2015 | Tucker et al. | |
| 9,918,687 B2 | 3/2018 | Nemoto | |
| 10,124,110 B2 | 11/2018 | Dedig et al. | |
| 10,201,666 B2 | 2/2019 | Cowan et al. | |
| 10,507,319 B2 | 12/2019 | Haury et al. | |
| 10,583,256 B2 | 3/2020 | Berry et al. | |
| 2001/0033372 A1* | 10/2001 | Dragotta | G01N 21/51 356/239.5 |
| 2007/0299687 A1* | 12/2007 | Palmer | G16H 10/60 705/2 |
| 2008/0191013 A1 | 8/2008 | Liberatore | |
| 2012/0185267 A1* | 7/2012 | Kamen | A61B 5/0024 705/2 |
| 2013/0229344 A1* | 9/2013 | Ivanich | H04N 21/42204 345/156 |
| 2014/0115101 A1 | 4/2014 | Wittner et al. | |
| 2015/0209510 A1* | 7/2015 | Burkholz | G06F 3/011 604/93.01 |
| 2015/0274329 A1* | 10/2015 | Harp | A61J 1/22 53/474 |
| 2016/0203360 A1* | 7/2016 | Alvarez | G06V 40/28 345/156 |
| 2016/0213843 A1* | 7/2016 | Despa | G16H 20/17 |
| 2016/0228633 A1 | 8/2016 | Welsch et al. | |
| 2016/0331951 A1 | 11/2016 | Sokolov et al. | |
| 2017/0056604 A1* | 3/2017 | Cowan | A61M 5/007 |
| 2017/0106142 A1* | 4/2017 | Hochman | A61M 5/172 |
| 2017/0168688 A1* | 6/2017 | Yuds | G06V 40/172 |
| 2017/0245816 A1 | 8/2017 | Flohr et al. | |
| 2018/0140784 A1 | 5/2018 | Haverman et al. | |
| 2018/0161496 A1 | 6/2018 | Berry et al. | |

| | | | |
|---|---|---|---|
| 2019/0130792 A1* | 5/2019 | Rios | G09B 23/285 |
| 2019/0142274 A1 | 5/2019 | Addison et al. | |
| 2020/0066389 A1* | 2/2020 | Prince | A61M 5/31 |
| 2020/0237225 A1 | 7/2020 | Addison et al. | |
| 2020/0237237 A1 | 7/2020 | Mozdzierz | |
| 2020/0268281 A1 | 8/2020 | Jacquel et al. | |
| 2020/0289024 A1 | 9/2020 | Addison et al. | |
| 2020/0356249 A1* | 11/2020 | Hunter | G06V 40/20 |
| 2021/0142030 A1* | 5/2021 | Gupta | G06V 40/13 |
| 2021/0361863 A1* | 11/2021 | Burgess | A61M 5/145 |
| 2023/0173172 A1* | 6/2023 | Jubic | A61M 5/14566 382/103 |

FOREIGN PATENT DOCUMENTS

| | | | |
|---|---|---|---|
| CN | 207012242 U | 2/2018 | |
| CN | 207745385 U | 8/2018 | |
| JP | 2004289720 A | 10/2004 | |
| JP | 2005062994 A | 3/2005 | |
| JP | 4892564 B2 | 3/2012 | |
| WO | 2005076810 A2 | 8/2005 | |
| WO | 2014100687 A2 | 6/2014 | |
| WO | 2015117852 A1 | 8/2015 | |
| WO | 2016112163 A1 | 7/2016 | |
| WO | 2017040152 A1 | 3/2017 | |
| WO | 2017040154 A1 | 3/2017 | |
| WO | 2018075386 A1 | 4/2018 | |
| WO | 2019035986 A1 | 2/2019 | |
| WO | 2019199644 A1 | 10/2019 | |

OTHER PUBLICATIONS

Balakrishnan; et al, "Detecting Pulse from Head Motions in Video", IEEE Proceed CVPR, 2013, 3430-3437.

Booij; et al, "Accuracy of automated patient positioning in CT using a 3D camera for body contour detection", European Radiology, Oct. 10, 2018, 29, 2079-2088.

Chandler; David L., "Your vital signs, on camera: MIT team develops system for continuous medical monitoring using widely available video technology", MIT News, Massachusetts Institute of Technology, Oct. 4, 2010.

Dougherty; et al, "Using Google Glass in Nonsurgical Medical Settings: Systematic Review", JMIR Mhealth and Uhealth, 2017, vol. 5 Issue 10 e159, 1-22.

"FAST Integrated Workflow", Siemens Healthineers USA, 2019.

McCarthy; Colin., "Virtual reality enters the IR suite", Interventional News, Feb. 21, 2018.

Ozdogan; Hakan, "The future of healthcare: Smart sensors and digital biomarkers", Dec. 2019.

Ramamurthy; et al, "Integrating Patient Digital Photographs with Medical Imaging Examinations", J Digit Imaging, Feb. 14, 2013, 26, 875-885.

Wu Hao-Yu; et al, "Eulerian Video Magnification for Revealing Subtle Changes in the World", Jul. 4, 2012, vol. 31 No. 65, 18.

* cited by examiner

SYSTEM AND METHOD UTILIZING AN INTEGRATED CAMERA WITH A FLUID INJECTOR

CROSS REFERENCE TO RELATED APPLICATION

The present application is a U.S. national phase application under 35 U.S.C. § 371 of International Application No. PCT/US2020/061733, filed Nov. 23, 2020, and claims the benefit of U.S. Provisional Patent Application No. 62/939,878, filed on 25 Nov. 2019, the disclosures of which are incorporated in their entirety by reference.

BACKGROUND OF THE DISCLOSURE

Field of the Disclosure

The present disclosure relates generally to fluid injectors having one or more image capture devices for capturing images and/or videos of objects and/or individuals positioned near the fluid injectors and, more particularly, to fluid injectors having a camera for capturing images and/or videos of objects and/or individuals positioned near the fluid injectors.

Description of Related Art

In many medical diagnostic and therapeutic procedures, a medical practitioner injects a patient with one or more medical fluids. In recent years, a number of injector-actuated syringes and powered fluid injectors for pressurized injection of medical fluids, such as a contrast medium (often referred to simply as "contrast"), a flushing agent, such as saline, and other medical fluids, have been developed for use in contrast enhanced imaging procedures such as cardiovascular angiography (CV), computed tomography (CT), ultrasound, magnetic resonance imaging (MRI), positron emission tomography (PET), and other imaging procedures. In general, these fluid injectors are designed to deliver a preset amount of one or more fluids at a preset pressure and/or flow rate.

Typically, fluid injectors have at least one drive member, such as a piston, that connects to the syringe, for example via connection with a plunger or an engagement feature on a proximal end wall of the syringe. The syringe may include a rigid barrel with the syringe plunger being slidably disposed within the barrel. In some examples, the syringe may include a rolling diaphragm barrel configuration having a flexible sidewall configured to roll upon itself, where the proximal end wall of the syringe body releasably engages with the at least one drive member. The drive members drive the plungers or the rolling diaphragm/proximal end wall in a proximal and/or distal direction relative to a longitudinal axis of the barrel to draw fluid into or deliver the fluid from the syringe barrel.

Patients undergoing diagnostic imaging scans in a CT or MR environment using these fluid injectors often receive an injection of contrast media in order to enhance the acquired images. The injection of the contrast media must be closely coordinated with an image scanner so that the region of interest (ROI) is scanned as the contrast flows therethrough while minimizing both the amount of contrast being injected and the radiation to which the patient is exposed. Technologists that administer the image scan must be thoroughly trained to use the fluid injectors and the image scanner to proceed through multiple steps to prepare the patient and the equipment in order to start and complete the image scan.

In view of the foregoing, there is a current need in the art for a fluid injector having at least one image capture device to capture images and/or videos of a patient, a physician, or an operator in order to provide safety features and ease-of-use of the fluid injectors. There is also a current need in the art for a fluid injector having at least one image capture device that assists in authorizing individuals to use the fluid injector and to assist in recording information regarding the fluid being used in the fluid injector and events that occur while using the fluid injector.

SUMMARY OF THE DISCLOSURE

In view of the above-identified needs, provided is a system and method for utilizing at least one image capture device with a fluid injector. In some examples of the present disclosure, a fluid injector system configured for use in administering at least one fluid to a patient may include at least one image capture device configured for capturing image data in an environment surrounding the fluid injector system, and a control device comprising at least one processor programmed or configured to: receive, with the at least one processor, the image data captured by the at least one image capture device; determine, with the at least one processor, whether the received image data comprises at least one predetermined characteristic; and perform, with the at least one processor, at least one action in response to determining whether the received image data comprises at least one predetermined characteristic.

In some examples of the present disclosure, the at least one image capture device may be at least one camera. The at least one camera may be at least one of: a) integrally formed with an injector housing of the fluid injector system, and b) operatively connected to an injector housing of the fluid injector system via an extendable member that permits the at least one camera to be moved relative to the injector housing. The control device may be configured to: receive, from the at least one image capture device, facial identification information or biometric information regarding a user based on an image or a video of the user positioned near the fluid injector system, and compare the received facial identification or biometric identification information regarding the user to a stored facial identification information or biometric identification information to determine whether the user is an individual authorized to use the fluid injector system. The control device may be configured to activate the fluid injector system or operate the fluid injector system upon receiving a confirmed match between the received facial identification information or biometric identification information and the stored facial identification information or the biometric identification information. The control device may be configured to set the fluid injector system to a preferred user interface upon receiving a confirmed match between the received facial identification information or the biometric identification information and the stored facial identification information or the biometric identification information. The control device may be configured to retrieve credentials of the user to confirm that the user's credentials are up-to-date. The control device may be configured to: receive, from the at least one image capture device, facial identification information or biometric identification information regarding a patient based on an image or a video of the patient positioned near the fluid injector system, and retrieve patient records for the patient based on the facial identification information or the biometric identification information received by the control device regarding the patient. The at least one image capture device may be configured to capture at least one image of at least one of a label on an object, a barcode on the object, a color of the object, a color of a fluid contained in the object, a shape of the object, and a QR code of the object positioned near an injector housing of the fluid injector system. The control device may be configured to automatically document details regarding the object based on the shape, the color, the label, the barcode, or the QR code captured by the at least one image capture device. The control device may be configured to forward information regarding the object identified by the at least one image capture device to a central database to assist in inventory tracking of the object. A projection system may be provided on the injector housing of the fluid injector system, wherein the projection system is configured to display information on at least one syringe held in the fluid injector system corresponding to the object identified by the at least one image capture device. The at least one image capture device may be configured to capture an image or a video of at least one hand gesture performed by an individual positioned near the fluid injector system, wherein the control device is configured to receive hand gesture identification information from the at least one image capture device based on the at least one hand gesture performed by the individual, and wherein the control device is configured to conduct a predetermined operation based on the hand gesture identification information received from the at least one image capture device. A near-infrared projection system that is configured to perform at least one of: a) vein mapping on a patient positioned near the fluid injector system, wherein the at least one image capture device is configured to capture at least one image or video of the vein mapping of the patient, and b) a pattern illumination on the patient's limb, wherein the at least one image capture device is configured to capture at least one image or video of the pattern illuminated on the patient's limb. The at least one image capture device may be positioned and configured to capture at least one image or video of at least one of: a) an insertion site of an intravenous needle on a patient positioned near the fluid injector system, and b) a patient positioned near the fluid injector system to detect a change in blood flow of the patient. The control device may be configured to record the at least one image data or video data in a central database for future review upon an adverse event occurring in connection with use of the fluid injector system.

In some examples of the present disclosure, a computer-implemented method for operating a fluid injector system configured for use in administering at least one fluid to a patient may include capturing, with at least one image capture device, image data in an environment surrounding the fluid injector system; receiving, with a control device comprising at least one processor, the image data captured by the at least one image capture device; determining, with the control device, whether the received image data comprises at least one predetermined characteristic; and performing, with the control device, at least one action in response to determining whether the received image data comprises at least one predetermined characteristic.

In some examples of the present disclosure, the at least one image capture device is at least one camera, wherein the at least one camera is at least one of: a) integrally formed with an injector housing of the fluid injector system, and b) operatively connected to an injector housing of the fluid injector system via an extendable member that permits the at least one camera to be moved relative to the injector housing. The method may include receiving, with the control device and from the at least one image capture device, facial identification information or biometric identification information regarding a user based on an image or a video of the user positioned near the fluid injector system, and comparing, using the control device, the received facial identification information or the biometric identification information regarding the user to a stored facial identification information or biometric identification information to determine whether the user is an individual authorized to use the fluid injector system. The method may include activating or operating, using the control device, the fluid injector system upon receiving a confirmed match between the received facial identification information or the biometric identification information and the stored facial identification information or biometric identification information. The method may include setting, using the control device, the fluid injector system to a preferred user interface upon receiving a confirmed match between the received facial identification information or biometric identification information and the stored facial identification information or biometric identification information. The method may include retrieving, using the control device, credentials of the user to confirm that the user's credentials are up-to-date. The method may include receiving, using the control device and from the at least one image capture device, facial identification information or biometric identification information regarding a patient based on an image or a video of the patient positioned near the fluid injector system, and retrieving, using the control device, patient records for the patient based on the facial identification information or biometric identification information received by the control device regarding the patient. The method may include capturing, with the at least one image capture device, at least one image of at least one of a label on an object, a barcode on the object, a color of the object, a color of a fluid contained in the object, a shape of the object, and a QR code of the object positioned near an injector housing of the fluid injector system. The method may include automatically documenting, using the control device, details regarding the object based on the shape, the color, the label, the barcode, or the QR code captured by the at least one image capture device. The method may include forwarding, using the control device, information regarding the object identified by the at least one image capture device to a central database to assist in inventory tracking of the object. The method may include providing a projection system provided on the injector housing of the fluid injector system, displaying, using the projection system, information on at least one syringe held in the fluid injector system corresponding to the object identified by the at least one image capture device. The method may include capturing, using the at least one image capture device, an image or a video of at least one hand gesture performed by an individual positioned near the fluid injector system, receiving, using the control device, hand gesture identification information from the at least one image capture device based on the at least one hand gesture performed by the individual, and conducting, using the control device, a predetermined operation based on the hand gesture identification information received from the at least one image capture device. The method may include providing a near-infrared projection system that is configured to perform at least one of: a) vein mapping on a patient positioned near the fluid injector system, and capturing, using the at least one image capture device, at least one image or video of the vein mapping of the patient, and b) pattern illumination on the patient's limb, wherein the at least one image capture device is configured to capture at least one image or video of the pattern illuminated on the patient's limb. The method may include positioning and configuring the at least one image capture device to capture at least one image or video of at least one of: a) an insertion site of an intravenous needle on a patient positioned near the fluid injector system, and b) a patient positioned near the fluid injector system to detect a change in blood flow of the patient. The method may include recording, using the control device, the image data in a central database for future review upon an adverse event occurring in connection with use of the fluid injector system.

In some examples of the present disclosure, a computer program product for operating a fluid injector system configured for use in administering at least one fluid to a patient, the computer program product may include at least one non-transitory computer-readable medium comprising one or more instructions that, when executed by at least one processor, cause the at least one processor to: capture, with at least one image capture device, image data in an environment surrounding the fluid injector system; receive the image data captured by the at least one image capture device; determine whether the received image data comprises at least one predetermined characteristic; and perform at least one action in response to determining whether the received image data comprises at least one predetermined characteristic.

In some examples of the present disclosure, the at least one image capture device is at least one camera, wherein the at least one camera is at least one of: a) integrally formed with an injector housing of the fluid injector system, and b) operatively connected to an injector housing of the fluid injector system via an extendable member that permits the at least one camera to be moved relative to the injector housing. The one or more instructions may further cause the at least one processor to: receive, with the control device and from the at least one image capture device, facial identification information or biometric identification information regarding a user based on an image or a video of the user positioned near the fluid injector system, and compare, using the control device, the received facial identification information or biometric identification information regarding the user to a stored facial identification information or biometric identification information to determine whether the user is an individual authorized to use the fluid injector system. The one or more instructions may further cause the at least one processor to activate or operate, using the control device, the fluid injector system upon receiving a confirmed match between the received facial identification information or biometric identification information and the stored facial identification information or biometric identification information. The one or more instructions may further cause the at least one processor to set, using the control device, the fluid injector system to a preferred user interface upon receiving a confirmed match between the received facial identification information or biometric identification information and the stored facial identification information or biometric identification information. The one or more instructions may further cause the at least one processor to retrieve, using the control device, credentials of the user to confirm that the user's credentials are up-to-date. The one or more instructions may further cause the at least one processor to: receive, using the control device and from the at least one image capture device, facial identification information or biometric identification information regarding a patient based on an image or a video of the patient positioned near the fluid injector system, and retrieve, using the control device, patient records for the patient based on the facial identification information or biometric identification information received by the control device regarding the patient. The one or more instructions may further cause the at least one processor to capture, with the at least one image capture device, at least one image of at least one of a label on an object, a barcode on the object, a color of the object, a color of a fluid contained in the object, a shape of the object, and a QR code of the object positioned near an injector housing of the fluid injector system. The one or more instructions may further cause the at least one processor to automatically document, using the control device, details regarding the object based on the shape, the color, the label, the barcode, or the QR code captured by the at least one image capture device. The one or more instructions may further cause the at least one processor to forward, using the control device, information regarding the object identified by the at least one image capture device to a central database to assist in inventory tracking of the object. The fluid injector system may include a projection system provided on the injector housing of the fluid injector system, and wherein the one or more instructions further cause the at least one processor to display, using the projection system, information on at least one syringe held in the fluid injector system corresponding to the object identified by the at least one image capture device. The one or more instructions may further cause the at least one processor to: capture, using the at least one image capture device, an image or a video of at least one hand gesture performed by an individual positioned near the fluid injector system, receive, using the control device, hand gesture identification information from the at least one image capture device based on the at least one hand gesture performed by the individual, and conduct, using the control device, a predetermined operation based on the hand gesture identification information received from the at least one image capture device. The fluid injector system may include a near-infrared projection system that is configured to perform at least one of: a) vein mapping on a patient positioned near the fluid injector system, wherein the one or more instructions further cause the at least one processor to capture, using the at least one image capture device, at least one image or video of the vein mapping of the patient, and b) pattern illumination on the patient's limb, wherein one or more instructions further cause the at least one processor to capture, using the at least one image capture device, at least one image or video of the pattern illuminated on the patient's limb. The one or more instructions may further cause the at least one processor to configure the at least one image capture device to capture at least one image or video of at least one of: a) an insertion site of an intravenous needle on a patient positioned near the fluid injector system, and b) a patient positioned near the fluid injector system to detect a change in blood flow of the patient. The one or more instructions may further cause the at least one processor to record, using the control device, the image data in a central database for future review upon an adverse event occurring in connection with use of the fluid injector system.

The following clauses also recite further features of the present disclosure:

Clause 1: A fluid injector system configured for use in administering at least one fluid to a patient, the fluid injector system comprising: at least one image capture device configured for capturing image data in an environment surrounding the fluid injector system; and a control device comprising at least one processor programmed or configured to: receive, with the at least one processor, the image data captured by the at least one image capture device; determine, with the at least one processor, whether the received image data comprises at least one predetermined characteristic; and perform, with the at least one processor, at least one action in response to determining whether the received image data comprises at least one predetermined characteristic.

Clause 2: The fluid injector system of Clause 1, wherein the at least one image capture device is at least one camera, the at least one camera being at least one of: a) integrally formed with an injector housing of the fluid injector system, and b) operatively connected to an injector housing of the fluid injector system via an extendable member that permits the at least one camera to be moved relative to the injector housing.

Clause 3: The fluid injector system of Clause 1 or Clause 2, wherein the control device is configured to: receive, from the at least one image capture device, facial identification information or biometric information regarding a user based on an image or a video of the user positioned near the fluid injector system, and compare the received facial identification or biometric identification information regarding the user to a stored facial identification information or biometric identification information to determine whether the user is an individual authorized to use the fluid injector system.

Clause 4: The fluid injector system of Clause 3, wherein the control device is configured to activate the fluid injector system or operate the fluid injector system upon receiving a confirmed match between the received facial identification information or biometric identification information and the stored facial identification information or the biometric identification information.

Clause 5: The fluid injector system of Clause 3 or Clause 4, wherein the control device is configured to set the fluid injector system to a preferred user interface upon receiving a confirmed match between the received facial identification information or the biometric identification information and the stored facial identification information or the biometric identification information.

Clause 6: The fluid injector system of any of Clauses 3-5, wherein the control device is configured to retrieve credentials of the user to confirm that the user's credentials are up-to-date.

Clause 7: The fluid injector system of any of Clauses 1-6, wherein the control device is configured to: receive, from the at least one image capture device, facial identification information or biometric identification information regarding a patient based on an image or a video of the patient positioned near the fluid injector system, and retrieve patient records for the patient based on the facial identification information or the biometric identification information received by the control device regarding the patient.

Clause 8: The fluid injector system of any of Clauses 1-7, wherein the at least one image capture device is configured to capture at least one image of at least one of a label on an object, a barcode on the object, a color of the object, a color of a fluid contained in the object, a shape of the object, and a QR code of the object positioned near an injector housing of the fluid injector system.

Clause 9: The fluid injector system of Clause 8, wherein the control device is configured to automatically document details regarding the object based on the shape, the color, the label, the barcode, or the QR code captured by the at least one image capture device.

Clause 10: The fluid injector system of Clause 8 or Clause 9, wherein the control device is configured to forward information regarding the object identified by the at least one image capture device to a central database to assist in inventory tracking of the object.

Clause 11: The fluid injector system of any of Clauses 8-10, further comprising a projection system provided on the injector housing of the fluid injector system, wherein the projection system is configured to display information on at least one syringe held in the fluid injector system corresponding to the object identified by the at least one image capture device.

Clause 12: The fluid injector system of any of Clauses 1-11, wherein the at least one image capture device is configured to capture an image or a video of at least one hand gesture performed by an individual positioned near the fluid injector system, wherein the control device is configured to receive hand gesture identification information from the at least one image capture device based on the at least one hand gesture performed by the individual, and wherein the control device is configured to conduct a predetermined operation based on the hand gesture identification information received from the at least one image capture device.

Clause 13: The fluid injector system of any of Clauses 1-12, further comprising a near-infrared projection system that is configured to perform at least one of: a) vein mapping on a patient positioned near the fluid injector system, wherein the at least one image capture device is configured to capture at least one image or video of the vein mapping of the patient, and b) a pattern illumination on the patient's limb, wherein the at least one image capture device is configured to capture at least one image or video of the pattern illuminated on the patient's limb.

Clause 14: The fluid injector system of any of Clauses 1-13, wherein the at least one image capture device is positioned and configured to capture at least one image or video of at least one of: a) an insertion site of an intravenous needle on a patient positioned near the fluid injector system, and b) a patient positioned near the fluid injector system to detect a change in blood flow of the patient.

Clause 15: The fluid injector system of any of Clauses 1-14, wherein the control device is configured to record the at least one image data or video data in a central database for future review upon an adverse event occurring in connection with use of the fluid injector system.

Clause 16: A computer-implemented method for operating a fluid injector system configured for use in administering at least one fluid to a patient, the method comprising: capturing, with at least one image capture device, image data in an environment surrounding the fluid injector system; receiving, with a control device comprising at least one processor, the image data captured by the at least one image capture device; determining, with the control device, whether the received image data comprises at least one predetermined characteristic; and performing, with the control device, at least one action in response to determining whether the received image data comprises at least one predetermined characteristic.

Clause 17: The computer-implemented method of Clause 16, wherein the at least one image capture device is at least one camera, wherein the at least one camera is at least one of: a) integrally formed with an injector housing of the fluid injector system, and b) operatively connected to an injector housing of the fluid injector system via an extendable member that permits the at least one camera to be moved relative to the injector housing.

Clause 18: The computer-implemented method of Clause 16 or Clause 17, further comprising: receiving, with the control device and from the at least one image capture device, facial identification information or biometric identification information regarding a user based on an image or a video of the user positioned near the fluid injector system, and comparing, using the control device, the received facial identification information or the biometric identification information regarding the user to a stored facial identification information or biometric identification information to determine whether the user is an individual authorized to use the fluid injector system.

Clause 19: The computer-implemented method of Clause 18, further comprising activating or operating, using the control device, the fluid injector system upon receiving a confirmed match between the received facial identification information or the biometric identification information and the stored facial identification information or biometric identification information.

Clause 20: The computer-implemented method of Clause 18 or Clause 19, further comprising setting, using the control device, the fluid injector system to a preferred user interface upon receiving a confirmed match between the received facial identification information or biometric identification information and the stored facial identification information or biometric identification information.

Clause 21: The computer-implemented method of any of Clauses 18-20, further comprising retrieving, using the control device, credentials of the user to confirm that the user's credentials are up-to-date.

Clause 22: The computer-implemented method of any of Clauses 16-21, further comprising: receiving, using the control device and from the at least one image capture device, facial identification information or biometric identification information regarding a patient based on an image or a video of the patient positioned near the fluid injector system, and retrieving, using the control device, patient records for the patient based on the facial identification information or biometric identification information received by the control device regarding the patient.

Clause 23: The computer-implemented method of any of Clauses 16-22, further comprising capturing, with the at least one image capture device, at least one image of at least one of a label on an object, a barcode on the object, a color of the object, a color of a fluid contained in the object, a shape of the object, and a QR code of the object positioned near an injector housing of the fluid injector system.

Clause 24: The computer-implemented method of Clause 23, further comprising automatically documenting, using the control device, details regarding the object based on the shape, the color, the label, the barcode, or the QR code captured by the at least one image capture device.

Clause 25: The computer-implemented method of Clause 23 or Clause 24, further comprising forwarding, using the control device, information regarding the object identified by the at least one image capture device to a central database to assist in inventory tracking of the object.

Clause 26: The computer-implemented method of any of Clauses 23-25, further comprising, providing a projection system provided on the injector housing of the fluid injector system, displaying, using the projection system, information on at least one syringe held in the fluid injector system corresponding to the object identified by the at least one image capture device.

Clause 27: The computer-implemented method of any of Clauses 16-26, further comprising: capturing, using the at least one image capture device, an image or a video of at least one hand gesture performed by an individual positioned near the fluid injector system, receiving, using the control device, hand gesture identification information from the at least one image capture device based on the at least one hand gesture performed by the individual, and conducting, using the control device, a predetermined operation based on the hand gesture identification information received from the at least one image capture device.

Clause 28: The computer-implemented method of any of Clauses 16-27, further comprising providing a near-infrared projection system that is configured to perform at least one of: a) vein mapping on a patient positioned near the fluid injector system, and capturing, using the at least one image capture device, at least one image or video of the vein mapping of the patient, and b) pattern illumination on the patient's limb, wherein the at least one image capture device is configured to capture at least one image or video of the pattern illuminated on the patient's limb.

Clause 29: The computer-implemented method of any of Clauses 16-28, further comprising positioning and configuring the at least one image capture device to capture at least one image or video of at least one of: a) an insertion site of an intravenous needle on a patient positioned near the fluid injector system, and b) a patient positioned near the fluid injector system to detect a change in blood flow of the patient.

Clause 30: The computer-implemented method of any of Clauses 16-29, further comprising recording, using the control device, the image data in a central database for future review upon an adverse event occurring in connection with use of the fluid injector system.

Clause 31: A computer program product for operating a fluid injector system configured for use in administering at least one fluid to a patient, the computer program product comprising at least one non-transitory computer-readable medium comprising one or more instructions that, when executed by at least one processor, cause the at least one processor to: capture, with at least one image capture device, image data in an environment surrounding the fluid injector system; receive the image data captured by the at least one image capture device; determine whether the received image data comprises at least one predetermined characteristic; and perform at least one action in response to determining whether the received image data comprises at least one predetermined characteristic.

Clause 32: The computer program product of Clause 31, wherein the at least one image capture device is at least one camera, wherein the at least one camera is at least one of: a) integrally formed with an injector housing of the fluid injector system, and b) operatively connected to an injector housing of the fluid injector system via an extendable member that permits the at least one camera to be moved relative to the injector housing.

Clause 33: The computer program product of Clause 31 or Clause 32, wherein the one or more instructions further cause the at least one processor to: receive, with the control device and from the at least one image capture device, facial identification information or biometric identification information regarding a user based on an image or a video of the user positioned near the fluid injector system, and compare, using the control device, the received facial identification information or biometric identification information regarding the user to a stored facial identification information or biometric identification information to determine whether the user is an individual authorized to use the fluid injector system.

Clause 34: The computer program product of Clause 33, wherein the one or more instructions further cause the at least one processor to activate or operate, using the control device, the fluid injector system upon receiving a confirmed match between the received facial identification information or biometric identification information and the stored facial identification information or biometric identification information.

Clause 35: The computer program product of Clause 33 or Clause 34, wherein the one or more instructions further cause the at least one processor to set, using the control device, the fluid injector system to a preferred user interface upon receiving a confirmed match between the received facial identification information or biometric identification information and the stored facial identification information or biometric identification information.

Clause 36: The computer program product of any of Clauses 33-35, wherein the one or more instructions further cause the at least one processor to retrieve, using the control device, credentials of the user to confirm that the user's credentials are up-to-date.

Clause 37: The computer program product of any of Clauses 31-36, wherein the one or more instructions further cause the at least one processor to: receive, using the control device and from the at least one image capture device, facial identification information or biometric identification information regarding a patient based on an image or a video of the patient positioned near the fluid injector system, and retrieve, using the control device, patient records for the patient based on the facial identification information or biometric identification information received by the control device regarding the patient.

Clause 38: The computer program product of any of Clauses 31-37, wherein the one or more instructions further cause the at least one processor to capture, with the at least one image capture device, at least one image of at least one of a label on an object, a barcode on the object, a color of the object, a color of a fluid contained in the object, a shape of the object, and a QR code of the object positioned near an injector housing of the fluid injector system.

Clause 39: The computer program product of Clause 38, wherein the one or more instructions further cause the at least one processor to automatically document, using the control device, details regarding the object based on the shape, the color, the label, the barcode, or the QR code captured by the at least one image capture device.

Clause 40: The computer program product of Clause 38 or Clause 39, wherein the one or more instructions further cause the at least one processor to forward, using the control device, information regarding the object identified by the at least one image capture device to a central database to assist in inventory tracking of the object.

Clause 41: The computer program product of any of Clauses 38-40, wherein the fluid injector system further comprises a projection system provided on the injector housing of the fluid injector system, and wherein the one or more instructions further cause the at least one processor to display, using the projection system, information on at least one syringe held in the fluid injector system corresponding to the object identified by the at least one image capture device.

Clause 42: The computer program product of any of Clauses 31-41, wherein the one or more instructions further cause the at least one processor to: capture, using the at least one image capture device, an image or a video of at least one hand gesture performed by an individual positioned near the fluid injector system, receive, using the control device, hand gesture identification information from the at least one image capture device based on the at least one hand gesture performed by the individual, and conduct, using the control device, a predetermined operation based on the hand gesture identification information received from the at least one image capture device.

Clause 43: The computer program product of any of Clauses 31-42, wherein the fluid injector system further comprises a near-infrared projection system that is configured to perform at least one of: a) vein mapping on a patient positioned near the fluid injector system, wherein the one or more instructions further cause the at least one processor to capture, using the at least one image capture device, at least one image or video of the vein mapping of the patient, and b) pattern illumination on the patient's limb, wherein one or more instructions further cause the at least one processor to capture, using the at least one image capture device, at least one image or video of the pattern illuminated on the patient's limb.

Clause 44: The computer program product of any of Clauses 31-43, wherein the one or more instructions further cause the at least one processor to configure the at least one image capture device to capture at least one image or video of at least one of: a) an insertion site of an intravenous needle on a patient positioned near the fluid injector system, and b) a patient positioned near the fluid injector system to detect a change in blood flow of the patient.

Clause 45: The computer program product of any of Clauses 31-44, wherein the one or more instructions further cause the at least one processor to record, using the control device, the image data in a central database for future review upon an adverse event occurring in connection with use of the fluid injector system.

Further details and advantages of the various examples described in detail herein will become clear upon reviewing the following detailed description of the various examples in conjunction with the accompanying drawing figures.

DETAILED DESCRIPTION

Figure 1:
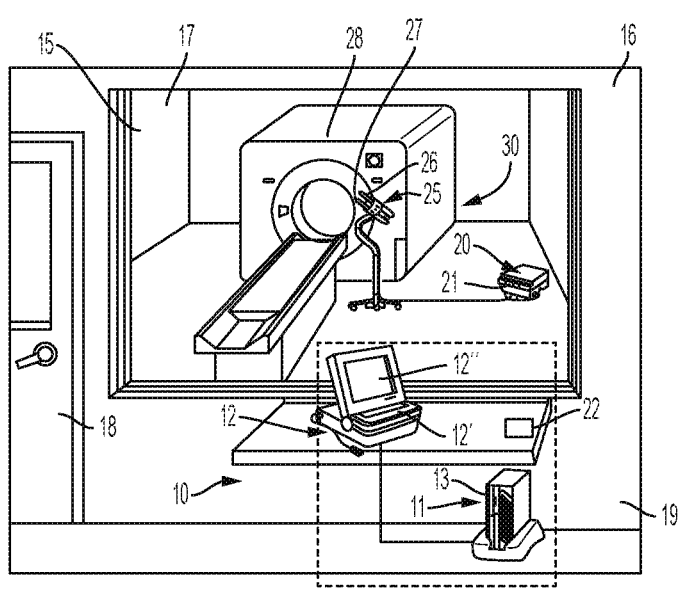
FIG. 1 is a perspective view of a magnetic resonance imaging (MRI) suite in which a fluid injector system is located in the scanner room and the controller therefor is located in the control room.

As used herein, the singular form of "a", "an", and "the" include plural referents unless the context clearly dictates otherwise.

Spatial or directional terms, such as "left", "right", "inner", "outer", "above", "below", and the like, relate to the invention as shown in the drawing figures and are not to be considered as limiting as the invention can assume various alternative orientations.

All numbers used in the specification and claims are to be understood as being modified in all instances by the term "about". The term "about" is meant to include plus or minus twenty-five percent of the stated value, such as plus or minus ten percent of the stated value. However, this should not be considered as limiting to any analysis of the values under the doctrine of equivalents.

Unless otherwise indicated, all ranges or ratios disclosed herein are to be understood to encompass the beginning and ending values and any and all subranges or sub-ratios subsumed therein. For example, a stated range or ratio of "1 to 10" should be considered to include any and all subranges or sub-ratios between (and inclusive of) the minimum value of 1 and the maximum value of 10; that is, all subranges or sub-ratios beginning with a minimum value of 1 or more and ending with a maximum value of 10 or less. The ranges and/or ratios disclosed herein represent the average values over the specified range and/or ratio.

The terms "first", "second", and the like are not intended to refer to any particular order or chronology, but refer to different conditions, properties, or elements.

All documents referred to herein are "incorporated by reference" in their entirety.

The term "at least" is synonymous with "greater than or equal to".

The term "not greater than" is synonymous with "less than or equal to".

As used herein, "at least one of" is synonymous with "one or more of". For example, the phrase "at least one of A, B, and C" means any one of A, B, or C, or any combination of any two or more of A, B, or C. For example, "at least one of A, B, and C" includes A alone; or B alone; or C alone; or A and B; or A and C; or B and C; or all of A, B, and C.

The term "includes" is synonymous with "comprises".

When used in relation to a syringe, for example a rolling diaphragm syringe, the term "proximal" refers to a portion of a syringe nearest a piston element for engaging with an end wall of the syringe and delivering fluid from a syringe. When used in relation to a fluid path, the term "proximal" refers to a portion of the fluid path nearest to an injector system when the fluid path is connecting with the injector system. When used in relation to a syringe, the term "distal" refers to a portion of a syringe nearest to an end thereof at which a delivery nozzle lies. When used in relation to a fluid path, the term "distal" refers to a portion of the fluid path nearest to a patient when the fluid path is connected with an injector system. The term "radial" refers to a direction in a cross-sectional plane normal to a longitudinal axis of a syringe extending between proximal and distal ends. The term "circumferential" refers to a direction around an inner or outer surface of a sidewall of a syringe. The term "axial" refers to a direction along a longitudinal axis of the syringe extending between the proximal and distal ends.

As used herein, the terms "communication" and "communicate" refer to the receipt or transfer of one or more signals, messages, commands, or other type of data. For one unit (e.g., any device, system, or component thereof) to be in communication with another unit means that the one unit is able to directly or indirectly receive data from and/or transmit data to the other unit. This may refer to a direct or indirect connection that is wired and/or wireless in nature. Additionally, two units may be in communication with each other even though the data transmitted may be modified, processed, relayed, and/or routed between the first and second unit. For example, a first unit may be in communication with a second unit even though the first unit passively receives data and does not actively transmit data to the second unit. As another example, a first unit may be in communication with a second unit if an intermediary unit processes data from one unit and transmits processed data to the second unit. It will be appreciated that numerous other arrangements are possible.

As used herein, the term "database" may refer to or include one or more processors or computers, storage devices, or similar computer arrangements that are operated by or facilitate communication and processing for multiple parties in a network environment, such as the Internet, although it will be appreciated that communication may be facilitated over one or more public or private network environments and that various other arrangements are possible. Further, multiple computers, e.g., servers, or other computerized devices, directly or indirectly communicating in the network environment may constitute a "system".

It is to be understood, however, that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the examples disclosed herein are not to be considered as limiting.

In some examples of the present disclosure, FIG. 1 illustrates a scanning suite showing the scanner room 15 in the background, the control room 19 in the foreground, and the electromagnetic shield 16 that completely surrounds the scanner room 15 and the magnetic resonance imaging (MRI) scanner 30 located within the scanner room 15. In some examples of the present disclosure, the scanning suite may be used for any of the following imaging environments: CT scans, MRI scans, PET scans, SPECT scans, U/S scans, IR scans, IC scans, X-Ray scans, mammography scans, and hybrid scans. The electromagnetic shield 16 is typically composed of a copper sheet material or some other suitable conductive layer such as wire mesh. In a wall of the electromagnetic shield 16, the MRI suite also includes a door 18 and, in one example of the present disclosure, a viewing window 17. The window 17 allows an observer and/or operator to see within the scanner room 15 without breaching the electromagnetic shield 16. The window 17 can be formed, for example, by sandwiching a wire mesh material (not shown) between sheets of glass or by coating the window 17 with a thin coating of conductive material, such as gold (not shown), to maintain the continuity of the electromagnetic shield 16. The conductive layer also extends to the door 18, which when open allows access to the scanner room 15 and yet when closed is grounded to and constitutes a part of the electromagnetic shield 16. The electromagnetic shield 16 constitutes an isolation barrier that attenuates RF signals. The roof, floors, walls and door 18 of shield 16 provide approximately 100 decibels (dB) of attenuation, and the window 17 approximately 80 dB. Consequently, communication through shield 16 is difficult without some means of conducting signals through this isolation barrier.

A fluid injector system is also provided in the scanner room 15, as shown in FIG. 1. The fluid injector system, for example, may be used to inject contrast media into the blood vessel of a patient undergoing an MRI procedure. In one example of the present disclosure, the fluid injector system may be the fluid injector system 100 described below. As is well known in the MRI field, the contrast media serves to increase the contrast between the different types of tissues in the region of the body undergoing the scan, and thereby enhance the resolution of the images obtained during the scanning procedure. The illustrated injection system includes a controller 10 in the control room 19 and the injection control unit 20 that it controls in the scanner room 15. The controller 10 features a processing unit 11 (e.g., a digital microcomputer), a battery charger 13, and an operator interface 12. The interface 12 may include, for example, a data entry unit 12' and a display 12". The controller 10 is situated outside of the scanner room 15 and thus away from the scanner 30, which is shielded from electromagnetic interference by shield 16. In one example of the present disclosure, the controller 10 may also include an MRI scanner operator interface 22 to operate the MRI scanner 30 from the control room 19. The controller 10 may also be used to operate and activate a camera (described below) provided on the fluid injector system. The controller 10 may also include a fingerprint reader to control use of the controller 10. In one example of the present disclosure, the fluid injector system may also include a temperature sensor to detect the temperature of the scanner room 15, a temperature of a fluid being injected into a patient, and/or a temperature of the patient.

The injection control unit 20 is preferably powered by a rechargeable battery 21. The injection head unit 25 may hold fluid containers 26 that deliver fluid to the patient. Separation of electric motors of the fluid injector system from an injection head 25, as well as additional electromagnetic shielding 27, results in improved performance of the fluid injector system and in improved quality of the images. The injection control unit 20 can be separated (for example, by ten to fifteen feet) from the injection head unit 25, which is typically placed near the patient. Although the injection control unit 20 is preferably shielded to prevent RF interference, ferromagnetic material in the injection control unit 20 can result in injection control unit 20 being drawn into the magnet gantry 28. This undesirable consequence can result in damage to the magnetic gantry 28, damage to the injection control unit 20, and/or injury to personnel present in the scanner room 15.

Referring to the drawings in which like reference characters refer to like parts throughout the several views thereof, one aspect or example of the present disclosure is generally directed to a multi-fluid medical injector/injector system 100 (hereinafter "fluid injector system 100") which in certain embodiments may include a multi-use disposable set (MUDS) 130 configured for delivering fluid to a patient using a single-use disposable set (SUDS) connector and in other embodiments may include two or more disposable fluid reservoirs or syringes, which may be disposed after one injection procedure or a specific number of injection procedures. The fluid injector system 100 may include multiple components as individually described herein. Generally, the fluid injector system 100 depicted in FIGS. 2 and 3 has a powered injector or other administration device and a fluid delivery set intended to be associated with the injector to deliver one or more fluids from one or more multi-dose containers under pressure into a patient, as described herein. The various devices, components, and features of the fluid injector system 100 and the fluid delivery set associated therewith are likewise described in detail herein. While the various examples of the methods and processes are shown with reference to an injector system having a multi-use disposable set ("MUDS") and a single-use disposable set ("SUDS") configuration in FIGS. 2 and 3, the disclosure is not limited to such an injector system and may be utilized in other syringe based injector systems, such as but not limited to those described in U.S. Pat. Nos. 7,553,294, 7,563,249, 8,945,051, 9,173,995, 10,124,110, 10,507,319, and 10,583, 256; and U.S. Patent Application Publication No. 2018-0161496; the disclosures of each of which are incorporated herein in their entirety by this reference.

Figure 2:
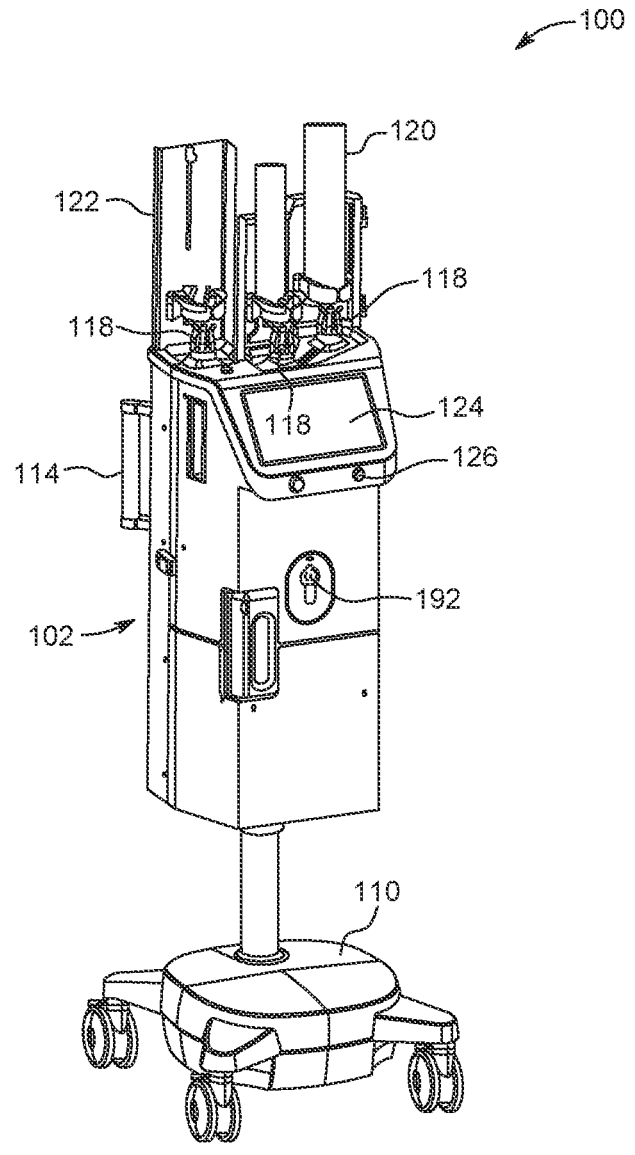
FIG. 2 is a perspective view of a fluid injector system according to one example of the present disclosure.

With reference to FIG. 2, a fluid injector system 100 according to one example includes an injector housing 102 that encloses the various mechanical drive components, electrical and power components necessary to drive the mechanical drive components, and control components, such as electronic memory and electronic control devices, used to control operation of reciprocally movable pistons (not shown) associated with the fluid injector system 100 described herein. Such pistons may be reciprocally operable via electro-mechanical drive components such as a ball screw shaft driven by a motor, a voice coil actuator, a rack-and-pinion gear drive, a linear motor, and the like. The fluid injector system 100 may include at least one handle 114 to move the fluid injector system 100.

The fluid injector system 100 may include at least one bulk fluid connector 118 for connection with at least one bulk fluid source 120. In some examples, a plurality of bulk fluid connectors 118 may be provided. For example, as shown in the fluid injector embodiment illustrated in FIG. 2, three bulk fluid connectors 118 may be provided in a side-by-side or other arrangement. In some examples, the at least one bulk fluid connector 118 may include a spike configured for removably connecting to the at least one bulk fluid source 120, such as a vial, a bottle, or a bag. The at least one bulk fluid connector 118 may be formed on the multi-use disposable set ("MUDS"), as described herein. The at least one bulk fluid source 120 may be configured for receiving a medical fluid, such as saline, Ringer's lactate, an imaging contrast medium solution, or other medical fluid, for delivery to the patient by the fluid injector system 100. The fluid sources 120 may be held on a manifold 122 of the fluid injector system 100.

Figure 3:
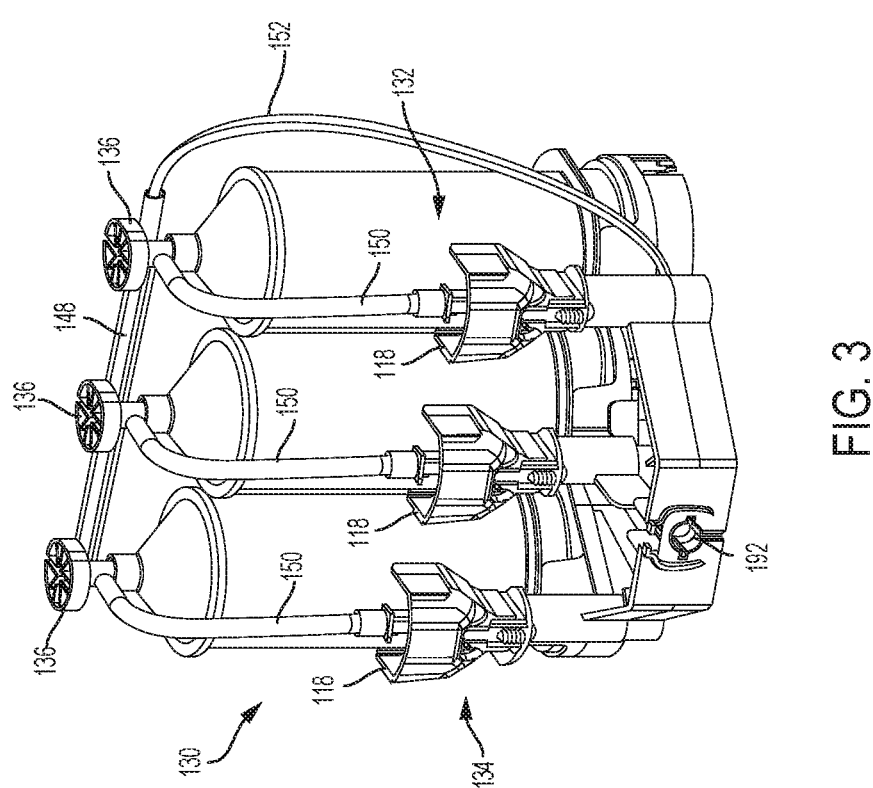
FIG. 3 is a perspective view of a multi-use disposable set for use with a fluid injector system of FIG. 2.

With reference to FIG. 3, a MUDS 130 is configured for being removably connected to the fluid injector system 100 for delivering one or more fluids from the one or more bulk fluid sources 120 to the patient. Examples and features of embodiments of the MUDS are further described in PCT International Publication No. WO 2016/112163, filed on Jan. 7, 2016, the disclosure of which is incorporated herein by reference in its entirety. The MUDS 130 may include one or more fluid reservoirs, such as one or more syringes 132. As used herein, the term "fluid reservoir" means any container capable of taking in and delivering a fluid, for example during a fluid injection procedure including, for example a syringe, a rolling diaphragm, a pump, a compressible bag, and the like. Fluid reservoirs may include the interior volume of at least a portion of a fluid pathway, such as one or more tubing lengths, that are in fluid communication with the interior of the fluid reservoir, including fluid pathway portions that remain in fluid communication with the fluid reservoir after the system is closed or fluidly isolated from the remainder of the fluid pathway. In some examples, the number of fluid reservoirs may correspond to the number of bulk fluid sources 120 (shown in FIG. 2). For example, with reference to FIG. 3, the MUDS 130 has three syringes 132 in a side-by-side arrangement such that each syringe 132 is fluidly connectable to one or more of the corresponding three bulk fluid sources 120. In some examples, one or more bulk fluid sources 120 may be connected to one or more syringes 132 of the MUDS 130. Each syringe 132 may be fluidly connectable to one of the bulk fluid sources 120 by a corresponding bulk fluid connector 118 and an associated MUDS fluid path 134. The MUDS fluid path 134 may have a spike element that connects to the bulk fluid connector 118 and the fluid line 150. In some examples, the bulk fluid connector 118 may be provided directly on the MUDS 130.

With continued reference to FIGS. 2 and 3, the MUDS 130 may include one or more valves 136, such as stopcock valves, for controlling which medical fluid or combinations of medical fluids are withdrawn from the multi-dose bulk fluid source 120 (see FIG. 2) into the fluid reservoirs 132 and/or are delivered to a patient from each fluid reservoir 132. In some examples, the one or more valves 136 may be provided on a distal end of the plurality of syringes 132 or on a manifold 148. The manifold 148 may be in selectable fluid communication via valves 136 with the interior volume of the syringes 132. The interior volume of the syringes 132 may be in selectable fluid communication via valves 136 with a first end of the MUDS fluid path 134 that connects each syringe 132 to the corresponding bulk fluid source 120. The opposing second end of the MUDS fluid path 134 may be connected to the respective bulk fluid connector 118 that is configured for fluidly connecting with the bulk fluid source 120. Depending on the position of the one or more valves 136, fluid may be drawn into the interior volume of the one or more syringes 132 or it may be delivered from the interior volume of the one or more syringes 132. In a first position, such as during the filling of the syringes 132, the one or more valves 136 are oriented such that fluid flows from the bulk fluid source 120 into the desired syringe 132 through a fluid inlet line 150, such as a MUDS fluid path. During the filling procedure, the one or more valves 136 are positioned such that fluid flow through one or more fluid outlet lines 152 or manifold 148 is blocked or closed. In a second position, such as during a fluid delivery procedure, fluid from one or more syringes 132 is delivered to the manifold 148 through the one or more fluid outlet lines 152 or syringe valve outlet ports. During the delivery procedure, the one or more valves 136 are positioned such that fluid flow through one or more fluid inlet lines 150 is blocked or closed. In a third position, the one or more valves 136 are oriented such that fluid flow through the one or more fluid inlet lines 150 and the one or more fluid outlet lines 152 or manifold 148 is blocked or closed. Thus, in the third position, each of the one or more valves 136 isolates the corresponding syringe 132 and prevents fluid flow into and out of the interior volume of the corresponding syringe 132. As such, each of the one or more syringes 132 and the corresponding valve 136 defines a closed system.

The one or more valves 136, fluid inlet lines 150, and/or fluid outlet lines 152 may be integrated into or in fluid communication via the manifold 148. The one or more valves 136 may be selectively positioned to the first or second position by manual or automatic handling. For example, the operator may position the one or more valves 136 into the desired position for filling, fluid delivery, or the closed position. In other examples, at least a portion of the fluid injector system 100 is operable for automatically positioning the one or more valves 136 into a desired position for filling, fluid delivery, or the closed position based on input by the operator or by a protocol executed by the electronic control unit.

With continued reference to FIGS. 2 and 3, according to the described embodiment the fluid injector system 100 may have a connection port 192 that is configured to form a releasable fluid connection with at least a portion of a single-use disposable set (not shown but referred to herein as "SUDS"). In some examples, the connection port 192 may be formed on the MUDS 130. As described herein, the SUDS may be connected to the connection port 192, formed on at least a portion of the MUDS 130 and/or the housing 102. Desirably, the connection between the SUDS and the connection port 192 is a releasable connection to allow the SUDS to be selectively connected to and disconnected from the connection port 192. In some examples, the SUDS may be disconnected from the connection port 192 and disposed after each fluid delivery procedure, and a new SUDS may be connected to the connection port 192 for a subsequent fluid delivery procedure. The SUDS may be used to deliver one or more medical fluids to a patient by SUDS fluid line 208 having a distal end that may be selectively disconnected from the body of the SUDS and connected to a patient catheter. Other examples and features of the SUDS are described in U.S. Patent Publication No. 2016/0331951, filed Jul. 7, 2016, the disclosure of which is incorporated herein by reference in its entirety.

Referring again to FIG. 2, the fluid injector system 100 may include one or more user interfaces 124, such as a graphical user interface (GUI) display window. The user interface 124 may display information pertinent to a fluid injection procedure involving fluid injector system 100, such as injection status or progress, current flow rate, fluid pressure, and volume remaining in the at least one bulk fluid source 120 connected to the fluid injector system 100 and may be a touch screen GUI that allows an operator to input commands and/or data for operation of fluid injector system 100. Additionally, the fluid injector system 100 and/or user interface 124 may include at least one control button 126 for tactile operation by an attendant operator of the fluid injector system 100. The at least one control button 126 may be a graphical part of the user interface 124, such as a touch screen.

Figure 4:
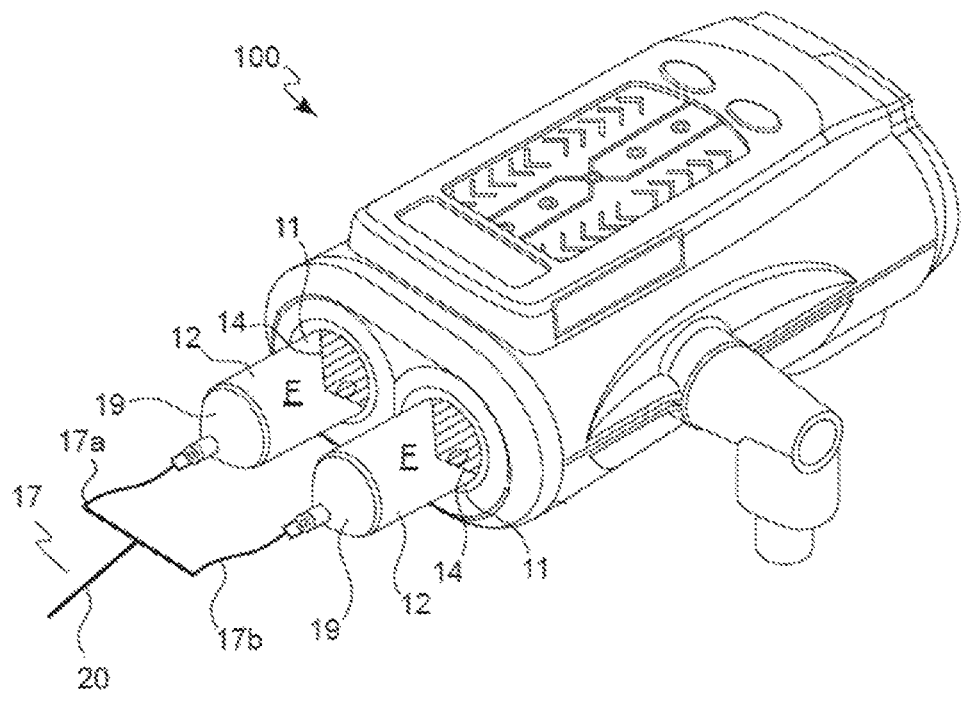
FIG. 4 is a perspective view of a fluid injector system according to another example of the present disclosure.

While FIGS. 2 and 3 illustrate one example of a fluid injector system 100 and associated components and structure, it is to be understood that the present disclosure is not limited to any particular type or variety of the fluid injector system 100. Referring now to FIG. 4, another non-limiting example of a fluid injector system 100 in accordance with the present disclosure includes at least one fluid reservoir, such as syringe 12, at least one piston connectable to at least one plunger 14, and a fluid control module (not pictured). The at least one syringe 12 is generally adapted to interface with at least one component of the system, such as a syringe port 13. The fluid injector system 100 is generally configured to deliver at least one fluid F to a patient during an injection procedure. The fluid injector system 100 is configured to releasably receive the at least one syringe 12, which is to be filled with at least one fluid F, such as a contrast media, saline solution, Ringer's lactate, or any desired medical fluid. The system may be a multi-syringe injector, wherein several syringes may be oriented side-by-side or in another spatial relationship and are separately actuated by respective pistons associated with the injector. The at least one syringe 12 may be oriented in any manner such as upright, downright, or positioned at any degree angle. In another embodiment, a fluid injector system 100 may interface with one or more rolling diaphragm syringes (not shown). Non-limiting examples of rolling diaphragm syringe based injectors are described in U.S. Pat. No. 10,583,256, U.S. Patent Application Publication No. 2018-0161496, and PCT International Application No. PCT/US2017/056747, the disclosures of which are incorporated herein.

With continued reference to FIG. 4, the injector system 100 may be used during a medical procedure to inject the at least one medical fluid F into the vasculature system of a patient by driving a plunger 14 of at least one syringe 12 with a drive member, such as the at least one piston. The at least one piston may be reciprocally operable upon at least a portion of the at least one syringe 12, such as the plunger 14. Upon engagement, the at least one piston may move the plunger 14 toward the distal end 19 of the at least one syringe 12, as well as retracting the plunger 14 toward the proximal end 11 of the at least one syringe 12.

A tubing set 17 (e.g., first and second fluid conduits 17a and 17b, and common fluid conduit 20) may be in fluid communication with an outlet port of each syringe 12 to place each syringe in fluid communication with a catheter for delivering the fluid F from each syringes 12 to the catheter (not shown) inserted into a patient at a vascular access site. The first and second fluid conduits 17a and 17b may be connected to the common fluid conduit 20 by any suitable mechanism known in the art (e.g., a Y-connector or a T-connector). The fluid injector system 100 shown in FIG. 4 is an open system due to the lack of valves capable of isolating the syringes 12 from one another and from at least a portion of the tubing set 17. However, it is to be understood that valves, similar or identical to the valves 136 described with reference to the fluid injector system 100 of FIGS. 2 and 3, may be added distally of the syringes 12 to convert the fluid injector system 100 of FIG. 4 to a closed system.

Figure 5:
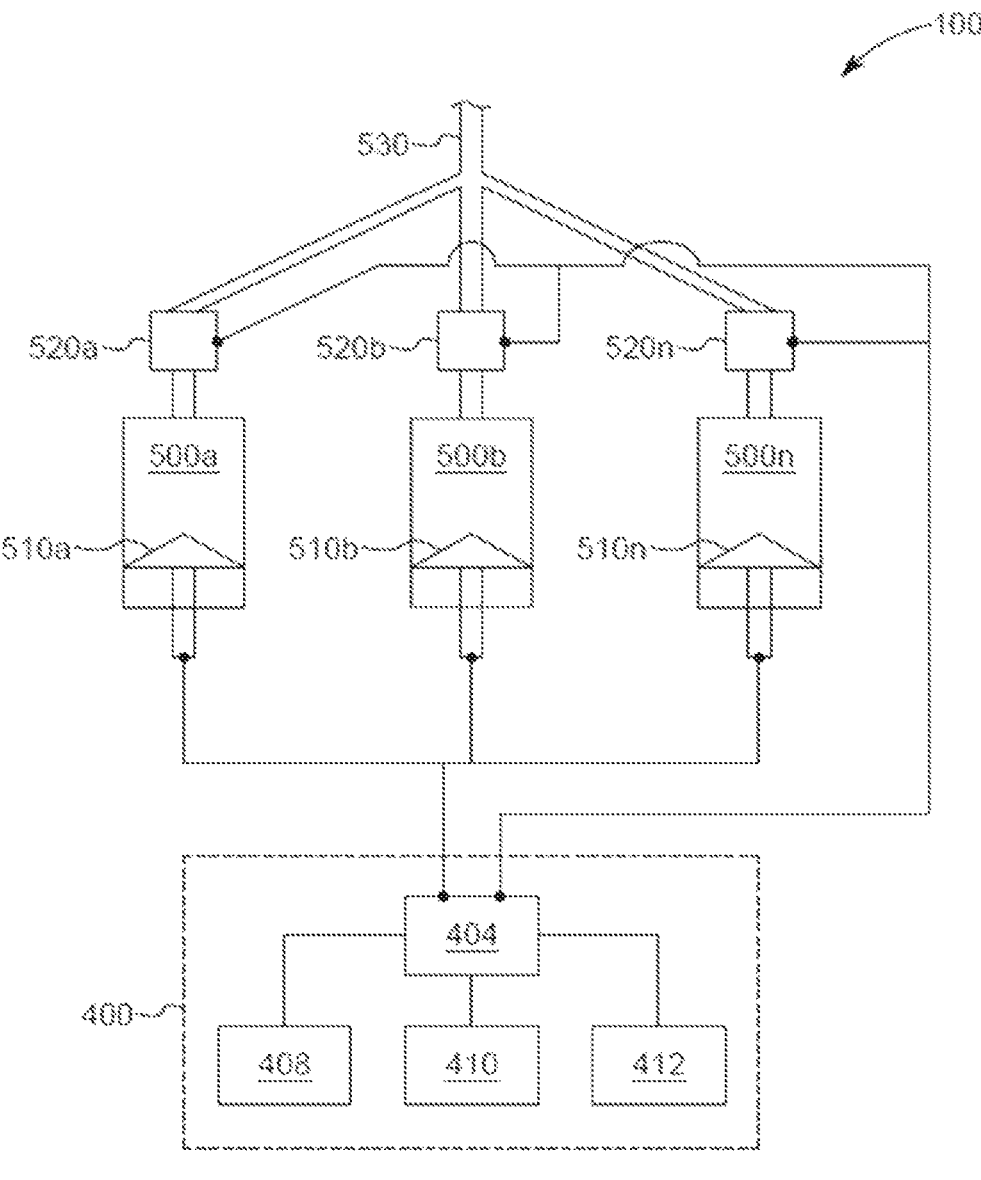
FIG. 5 is a schematic view of an electronic control system of a fluid injector system in accordance with examples of the present disclosure.

Referring now to FIG. 5, fluid injector systems 100 in accordance with the present disclosure may be associated with and controlled by an electronic control device 400 configured to execute one or more injector protocols including, for example, the filling, priming, and delivery operations. In some examples, the electronic control device 400 may control the operation of various valves, stopcocks, piston members, and other elements to affect a desired gas/air purging, priming, and/or delivery procedure. The electronic control device 400 may include at least one processor 404, memory 408, an input component 410, and an output component 412. The electronic control device further may include a bus that permits communication among the components of electronic control device 400. The at least one processor 404 may be implemented in hardware, firmware, or a combination of hardware and software. For example, processor 404 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 408 may include a hard disk (e.g., a magnetic disk, an optical disk, a magneto-optic disk, a solid state disk, etc.) and/or another type of computer-readable medium. The input component 410 may include a component that permits the electronic control device 400 to receive information, such as via user input (e.g., the user interface 124). The output component 412 may include a component that provides output information from the electronic control device 400 (e.g., the user interface 124).

The electronic control device 400 may be programmed or configured to perform one or more processes and/or methods based on the at least one processor 404 executing software instructions stored by a computer-readable medium, such as memory 408. When executed, software instructions stored in memory 408 may cause the at least one processor 404 to perform one or more processes and/or methods described herein.

With continued reference to FIG. 5, the electronic control device 400, more particularly the at least one processor 404, may be in operative communication with one or more components of the fluid injector system 100 to control an operation of the fluid injector system 100. The electronic control device 400 may be in operative communication with one or more drive components 510a, 510b, 510n respectively associated with one or more fluid reservoirs 500a, 500b, 500n of the fluid injector system 100 to control filling of fluid and delivery of fluid from the fluid reservoirs 500a, 500b, 500n. More particularly, each of the one or more drive components 510a, 510b, 510n may be associated with one of the fluid reservoirs 500a, 500b, 500n such that fluid contained in each of the fluid reservoirs 500a, 500b, 500n may be selectively delivered via actuation of the associated drive component 510a, 510b, 510n. The fluid reservoirs 500a, 500b, 500n may be, or may correspond to, the syringes 132 of the fluid injector system 100 of FIGS. 2 and 3 and/or the syringes 12 of the fluid injector system 100 of FIG. 4 or other syringe-type structures, such as rolling diaphragm syringes, as described herein. The one or more drive components 510a, 510b, 510n may be, or may correspond to, the pistons of the fluid injector systems 100 of FIGS. 2-4. The one or more fluid reservoirs 500a, 500b, 500n may be in fluid communication with a fluid conduit 530 for delivering fluid to a catheter or other component connected to a patient. The fluid conduit 530 may be, or may correspond to, the SUDS of the fluid injector system 100 of FIGS. 2 and 3 and/or the tubing set 17 of the fluid injector system 100 of FIG. 4.

In aspects and examples of a closed fluid injector system 100 (e.g., the fluid injector system 100 of FIGS. 2 and 3), the electronic control device 400 further may be in operative communication with one or more valves 520a, 520b, 520n in order to rotate or otherwise actuate the valves 520a, 520b, 520n to direct flow into or out of and/or isolate flow from one or more of the fluid reservoirs 500a, 500b, 500n to the fluid conduit 530. The valves 520a, 520b, 520n may be, or may correspond to, the valves 136 described herein in connection with FIG. 3.

In some aspects and examples, the at least one processor 404 may be programmed or configured to execute an injection protocol including a first phase and at least a second phase. Each of the first phase and the second phase of the injection protocol include or define a desired steady-state ratio of a first fluid relative to a second fluid. According to various embodiments, the steady-state ratio for each phase may range from 100:0 of the first fluid to the second fluid to 0:100 of the first fluid to the second fluid, inclusive of any intermediate ratios. As described herein, the desired steady-state ratio is based on volume component of the first fluid relative to the volume component of the second fluid, although mass, density, viscosity, flow rate, or another characteristic of the fluids may also be the basis of the desired steady-state ratio. According to certain embodiments, the first fluid may be an imaging contrast solution and the second fluid may be a flushing fluid, such as saline or Ringer's Lactate.

In some aspects or examples, the first fluid may be contained in a first fluid reservoir 500a and the second fluid may be contained in a second fluid reservoir 500b. It should be understood that the order of the various fluid reservoirs may be changed, for example, in certain embodiments the first fluid reservoir may be reservoir 500b and the second fluid reservoir may be 500a without deviating from the scope of the present disclosure. In certain embodiments, the third fluid reservoir 500n may contain a third fluid or an additional volume of the first or second fluids, or a different concentration of the first or second fluid. The desired steady-state ratios for the first and second phases of the injection protocol may be reached by selectively and independently actuating the first and second drive components 510a, 510b associated with the first and second fluid reservoir 500a, 500b and optionally actuating a third drive component 510n associated with a third fluid reservoir 500n. For example, if the desired steady-state ratio is 50% of the first fluid to 50% of the second fluid, the first and second drive components 510a, 510b associated with the first and second fluid reservoir 500a, 500b may be actuated, by the at least one processor 404, at the same speed to facilitate equal delivery of the first and second fluids. Similarly, if the desired steady-state ratio is 75% of the first fluid to 25% of the second fluid, the first drive component 510a associated with the first fluid reservoir 500a may be actuated at three times the speed of the second drive component 510b associated with the second fluid reservoir 500b to facilitate delivery of a 3:1 ratio of the first fluid relative to the second fluid. If the desired steady-state ratio is 100% of the first fluid to 0% of the second fluid, the first drive component 510a associated with the first fluid reservoir 500a is actuated and the second drive component 510b associated with the second fluid reservoir 500b is not actuated. In aspects or examples of the present disclosure, the first fluid may be contrast or another diagnostic imaging fluid, and the second fluid may be a diluent such as saline, Ringer's lactate, a mixture of contrast diluted with saline, or the like. The terms "contrast" and "diluent" may be used herein to refer to the first fluid and second fluid, respectively, when describing specific aspects or examples of the present disclosure. However, it is to be understood that aspects or examples of the present disclosure are not limited to using contrast and diluent as the first and second fluids.

Figure 6:
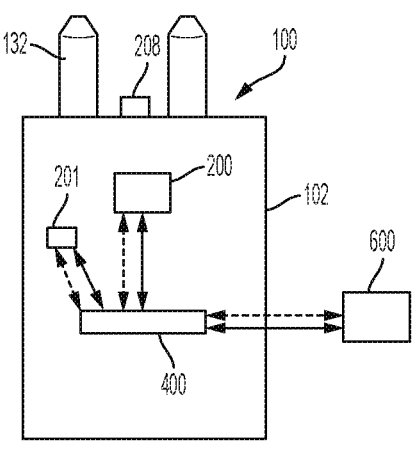
FIG. 6 is a schematic view of an image capture device operatively connected to a fluid injector system in accordance with some non-limiting examples of the present disclosure.

With reference to FIG. 6, in an example of the present disclosure, the fluid injector system 100 may include at least one image capture device 200 that is configured to capture image data and/or video data of objects and/or individuals positioned within the vicinity of the fluid injector system 100. In some examples of the present disclosure, the fluid injector system 100 may have at least two image capture devices 200. In some examples of the present disclosure, the image capture device 200 may be an infrared camera, a visual camera, a stereoscopic camera, a thermal camera, a color camera, a black & white camera, or a magnetic resonance compatible camera. In some examples of the present disclosure, one image capture device 200 may be operatively connected to the fluid injector system 100. In some examples of the present disclosure, more than one image capture device may be operatively connected to the fluid injector system 100. In some examples of the present disclosure, the image capture device 200 may be a photo camera. In some examples of the present disclosure, the image capture device 200 may be a video camera. In some examples of the present disclosure, the image capture device 200 may be a combined photo and video camera. In some examples of the present disclosure, additional sensors 201 may be used in conjunction with the image capture device 200 to assist in use of the fluid injector system 100. For example, the sensors 201 may include optical sensors, ultrasonic sensors, and/or capacitive detection systems that may add additional features to the fluid injector system 100 such as automatic dimming of the fluid injector system's 100 user interface 124 as ambient light is reduced in the area of the fluid injector system 100, among other power saving actions performed by the fluid injector system 100. In some examples of the present disclosure, the image capture device 200 may be operated to capture images and/or videos using several different methods, including automated tracking programs included in the image capture device 200, fixed positioning, variable positioning in which the image capture device 200 periodically moves between several different positions, remote control operation, a fixed focus operation program, and an automated focus operation program.

In some examples of the present disclosure, the image capture device 200 may be configured to capture image data and/or video data of an object and/or an individual within an image detection field associated with the fluid injector system 100. The image capture device 200 may be configured to capture image data and/or video data of an object and/or an individual that is in line of sight of the image capture device 200. For example, the image capture device 200 may be configured to capture image/video data within at least 5 meters of the fluid injector system 100. In another example of the present disclosure, the image capture device 200 may be configured to capture image/video data within at least 2 meters of the fluid injector system 100. In one example of the present disclosure, the image capture device 200 may be configured to capture image/video data up to 10 meters from the fluid injector system 100. It is to be understood, however, that the image capture device 200 may also be configured to capture images and/or videos from a shorter distance or a longer distance than 5 meters. The image capture device 200 may be operatively connected to the electronic control device 400 of the fluid injector system 100. In some examples of the present disclosure, the image capture device 200 may be directly connected via wiring to the electronic control device 400. In some examples of the present disclosure, the image capture device 200 may be wirelessly connected to the electronic control device 400 using a WiFi connection, a Bluetooth connection, or any other wireless connection. In some examples of the present disclosure, the image processing initiated for the image data and/or video data captured by the image capture device 200 may be conducted using programming in the image capture device 200, an external location such as a control room, and/or external remote location accessed by a cloud processing system. In some examples of the present disclosure, the image capture device 200 may be continuously streaming the captured image data and/or video, the image capture device 200 may periodically capture image data and/or video data, and/or the image capture device 200 may only capture image data and/or video data upon detecting motion surrounding the fluid injector system 100. In some examples of the present disclosure, the image capture device 200 may be configured to automatically delete captured image data and/or video data periodically in the event the image data and/or video data is not used by the fluid injector system 100.

As shown in FIG. 6, in some examples of the present disclosure, the image capture device 200 may be formed integrally with the injector housing 102 of the fluid injector system 100. The image capture device 200 may be held in an opening defined in a front face of the injector housing 102 so that the image capture device 200 is directed to capture images and/or videos of objects and/or individuals positioned in front of the fluid injector system 100. In some examples of the present disclosure, the image capture device 200 may be held in the scanner 30 illustrated in FIG. 1. In some examples of the present disclosure, the image capture device 200 may be positioned in a ceiling of the scanner room 15.

Figure 7:
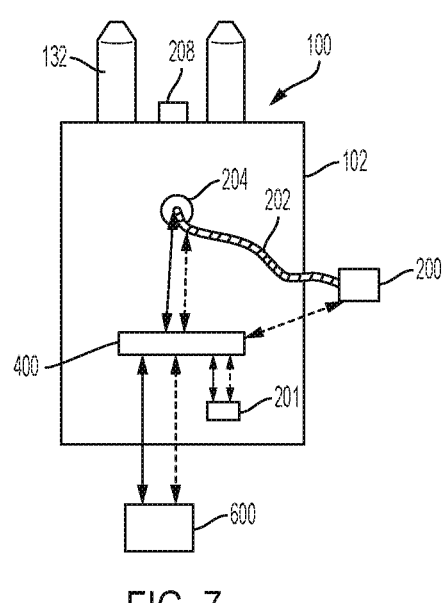
FIG. 7 is a schematic view of an image capture device operatively connected to a fluid injector system in accordance with some non-limiting examples of the present disclosure.

As shown in FIG. 7, in some examples of the present disclosure, the image capture device 200 may be operatively connected to the injector housing 102 of the fluid injector system 100 using an extendable member 202. In some examples, the image capture device 200 may be connected to one end of the extendable member 202 and the injector housing 102 may be connected to an opposing end of the extendable member 202. The extendable member 202 may be a cable member that holds wiring to operatively connect the image capture device 200 to the electronic control device 400 of the fluid injector system 100. In some examples, the image capture device 200 may be indirectly connected to the electronic control device 400 using a wireless connection using, for example, WiFi or Bluetooth. In some examples of the present disclosure, the image capture device 200 may be installed on a mobile device, such as a phone, held by the physician or technician. In some examples of the present disclosure, the image capture device 200 may also be installed on wearable tech devices for the physician or the technician, such as glasses or a bodycam. In some examples of the present disclosure, the image capture device 200 may be held on a patient in the scanner room 15. In some examples of the present disclosure, the image capture device 200 may be held on a patient table in the scanner room 15. In some examples of the present disclosure, the image capture device 200 may be positioned in a waiting room outside of the scanner room 15. In some examples of the present disclosure, the image capture device 20 may be fixed to a piece of furniture in the scanner room 15. In some examples of the present disclosure, the image capture device 200 may be mounted to a movable object, such as a drone, so that the image capture device 200 may be moved around the scanner room 15. The image capture device 200 may be docked in a base 204 defined in the injector housing 102. When in use, an operator or physician will be able to move the image capture device 200 relative to the injector housing 102 due to the extendable member 202. In this example, the operator or physician can position the image capture device 200 in a number of different positions relative to the injector housing 102. The extendable member 202 may be configured to extend and retract from the injector housing 102 to permit the image capture device 200 to be moved to a number of positions relative to the injector housing 102.

Figure 8:
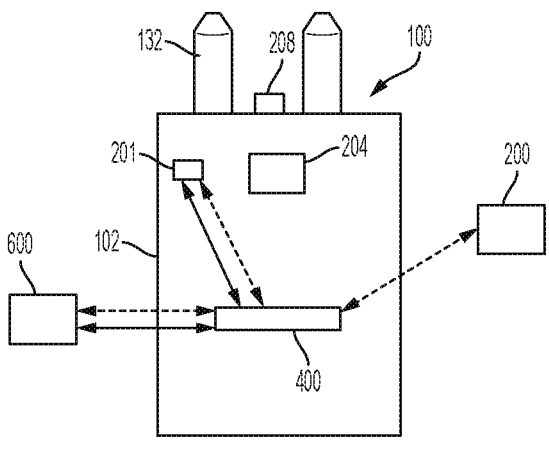
FIG. 8 is a schematic view of an image capture device operatively connected to a fluid injector system in accordance with some non-limiting examples of the present disclosure.

As shown in FIG. 8, in some examples of the present disclosure, the image capture device 200 may be operatively connected to the electronic control device 400 using a wireless connection via WiFi or Bluetooth. In some examples, the image capture device 200 may be docked in the aperture 204 defined in the injector housing 102. When in use, an operator or physician will be able to remove the image capture device 200 from the aperture 204 to move the image capture device 200 relative to the injector housing 102. In this example, the operator or physician can position the image capture device 200 in a number of different positions relative to the injector housing 102. When the operator or physician is done using the image capture device 200, the image capture device 200 may be docked back into the base 204 until the next time the image capture device 200 needs to be used.

Several different methods of using the image capture device 200 and the electronic control device 400 with the fluid injector system 100 are described. It is to be understood that these programs and methods may be performed using any of the image capture devices 200 described in connection with and illustrated in FIGS. 6-8. In the following description, the image capture device 200 may be configured to capture image data and/or video data of an individual or an object to identify a predetermined characteristic of the individual or the object.

Figure 9:
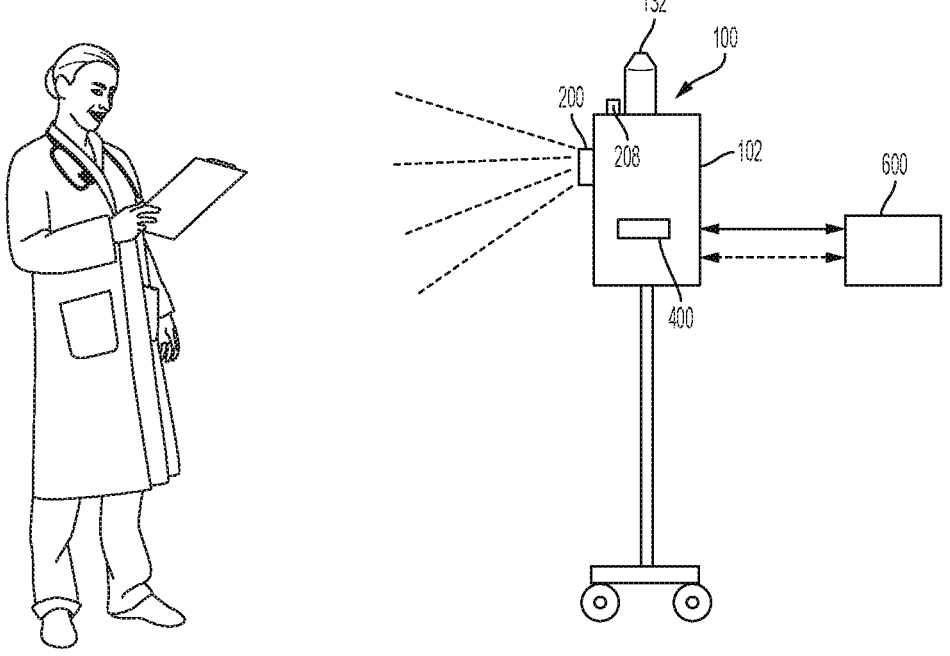
FIG. 9 is a schematic view of a fluid injector system including an image capture device capturing facial identification information of an individual in accordance with some non-limiting examples of the present disclosure.

With reference to FIG. 9, in some examples of the present disclosure, an operation of the image capture device 200 and the fluid injector system 100 is shown and described wherein the image capture device 200 and the electronic control device 400 may be configured and programmed to perform facial recognition or biometric recognition of an individual positioned near the fluid injector system 100. The image capture device 200 may be used throughout an entire scanning procedure with a patient, including the scheduling of the scanning procedure, to admission of the patient for the scanning procedure, to preparation for the scanning procedure to the scanning procedure itself, and to the post scanning procedure evaluation. The use of facial recognition with the fluid injector system 100 improves the safety and drives compliance of the fluid injector system 100 by restricting access to the fluid injector system 100 to only authorized physicians and technicians. It is to be understood that the following description describes the use of facial recognition with the image capture device 200, but the same methods may be used for biometric recognition with the image capture device 200.

In some examples of the present disclosure, the image capture device 200 may be configured to capture image data and/or video data regarding the individual positioned near the fluid injector system 100. For example, the image capture device 200 may be configured to take a photograph or video of a patient, a physician, or a technician that is positioned near the fluid injector system 100. The image data and/or the video data captured by the image capture device 200 may include facial identification information regarding the individual that is sent to the electronic control device 400 of the fluid injector system 100 via a wired or a wireless communication. Once the electronic control device 400 receives the facial identification information, the electronic control device 400 may be configured and programmed to compare the facial identification information to facial identification information stored either in the electronic control device 400 or a central database 600 in communication with the electronic control device 400.

In some examples of the present disclosure, upon receiving a positive match between the facial identification information captured by the image capture device 200 and the stored facial identification information, the fluid injector system 100 may be activated and unlocked for use by the physician or the technician. In some examples of the present disclosure, upon receiving a negative match between the facial identification information captured by the image capture device 200 and the stored facial identification information, the fluid injector system 100 may remain inactive and locked to prevent use by the physician or the technician. For example, in the event the photograph or video of the individual captured by the image capture device 200 matches the photograph or video of the individual stored in the electronic control device 400 or the central database 600, the fluid injector system 100 is activated and unlocked for use by the individual since this individual is authorized to use the fluid injector system 100. In the event the photograph or video of the individual captured by the image capture device 200 does not match the photograph or video of the individual stored in the electronic control device 400 or the central database 600, the fluid injector system 100 will remain inactive and locked to prevent use by the individual since this individual is not authorized to use the fluid injector system 100. In some examples, the owner of the fluid injector system 100 may store facial identification information in the electronic control device 400 or the central database 600 for a service engineer that may need access to the fluid injector system 100 for repairs or maintenance. Once the service engineer has worked on the fluid injector system 100, the facial identification information for this service engineer may be removed from the electronic control device 400 or the central database 600. In some examples of the present disclosure, in the event a positive match is identified, the individual may be granted partial access to the operation of the fluid injector system 100 that permits the individual to conduct certain task with the fluid injector system 100, but is not permitted to use all features of the fluid injector system 100.

In some examples of the present disclosure, the facial identification information captured by the image capture device 200 may be used to allow an authorized individual to create and save customized user interface preferences for the fluid injector system 100. The user interface preferences may be created based on the needs of the patient that is connected to the fluid injector system 100 or based on the personal operating preferences of the physician or technician. During use of the fluid injector system 100, the physician or the technician may change the user interface parameters of the fluid injector system 100. After the new user interface parameters have been entered by the physician or the technician, facial recognition may be performed by the image capture device 200 and the electronic control device 400 to save the customized user interface preferences to the profile of the particular physician or technician using the fluid injector system 100. For example, a physician or technician may set the user interface 124 of the fluid injector system 100 to a particular configuration, including adjusting the preferred protocols of the fluid injector system 100, the font size or style of the words and numbers displayed on the user interface 124 of the fluid injector system 100, the background screen brightness of the user interface 124, user preferences, tendencies, habits, and requirements for the fluid injector system 100, an operating mode (e.g. a simple-mode, a training-mode, or a power-mode) of the fluid injector system 100, volumes of the sounds issued by the fluid injector system 100, alert preferences for the fluid injector system 100, alarm preferences for the fluid injector system 100, and user feedback tones and volumes for the user interface 124, among other configuration settings. Once the preferred user interface configuration has been set on the fluid injector system 100, the electronic control device 400 may be configured to perform facial recognition for the physician to save the preferred user interface configuration to the physician's profile in the electronic control device 400 or the central database 600. After the preferred user interface configuration has been saved, the electronic control device 400 can set the user interface 124 of the fluid injector system 100 to the preferred user interface configuration for the physician the next time the physician uses the fluid injector system 100 based on facial recognition of the physician. A similar method and program may be used to save a preferred user interface configuration that is based on the particular patient using the fluid injector system 100. By using facial recognition of the patient, the electronic control device 400 can save the preferred user interface configuration set by the physician so that the next time the patient is identified with facial recognition, the electronic control device 400 will set the user interface 124 to the preferred user interface configuration saved for that particular patient.

In some examples of the present disclosure, the facial identification information captured by the image capture device 200 may be used by the electronic control device 400 to verify that a physician's or technician's training competencies for using the fluid injector system 100 are valid and up-to-date. The physician's and technician's training competencies, which may include reports indicating that the physician or technician has taken and passed training programs or modules for the fluid injector system 100, may be stored in the electronic control device 400 and/or the central database 600. After the image capture device 200 has captured the facial identification information, the facial identification information may be used by the electronic control device 400 to identify the physician or technician that is using the fluid injector system 100. Once the physician or the technician is identified, the electronic control device 400 may be configured to determine whether the physician's or technician's training competencies are valid and up-to-date to ensure the physician or the technician is competent in using the fluid injector system 100. In the event the physician's or the technician's training competencies are valid and up-to-date, the electronic control device 400 may be programmed to unlock the fluid injector system 100 and allow the physician or technician to operate the fluid injector system 100. In the event the physician's or the technician's training competencies are not valid and up-to-date, the electronic control device 400 may be programmed to lock the fluid injector system 100 from operation by the physician or the technician until it is established that the physician or the technician has achieved valid and up-to-date training competencies. In some examples of the present disclosure, the electronic control device 400 may also be programmed to notify the physician or the technician when his/her training competencies or credentials are close to expiring so the physician or the technician can schedule time to review and complete any new training programs or modules for the fluid injector system 100 to ensure his/her training competencies and credentials remain valid and up-to-date for using the fluid injector system 100.

In some examples of the present disclosure, the image capture device 200 and the electronic control device 400 may be used to perform facial recognition of an individual positioned near the fluid injector system 100 to activate or "wake" the fluid injector system 100 from a low-power state or resting state to a fully-operational state as the individual approaches the fluid injector system 100. Since each authorized individual will have been previously authenticated by the fluid injector system 100, the fluid injector system 100 may be configured and programmed to distinguish between an authorized physician or technician and unauthorized individuals that may be positioned near the fluid injector system 100, such as patients and custodians. As an individual is approaching the fluid injector system 100, the image capture device 200 may capture image data or video data of the approaching individual and the electronic control device 400 may perform facial recognition of the individual using the captured image data or video data. If the individual is authorized to use the fluid injector system 100, the electronic control device 400 will activate or "wake" the fluid injector system 100 so the fluid injector system 100 is ready for use once the individual reaches the fluid injector system 100. Otherwise, if the individual is not authorized to use the fluid injector system 100, the electronic control device 400 will not activate or "wake" the fluid injector system 100. By only switching the fluid injector system 100 to a full-power state upon recognition of an authorized individual, the overall fluid injector system 100 power may be conserved to increase workflow and efficiency since less down-time for the fluid injector system 100 is required to charge a battery for the fluid injector system 100.

In some examples of the present disclosure, if the individual is not authorized to use the fluid injector system 100, the fluid injector system 100 may be configured to lock the wheels of the base 110 so that the fluid injector system 100 may not be moved by the unauthorized individual. In some examples of the present disclosure, the image capture device 200 may be used to delay an injection procedure of the fluid injector system 100 or a scanning procedure of the scanner in the suite until the physician or the technician has left the scanning room. The image capture device 200 may be configured to capture image data and/or video data of the physician and/or the technician while he/she is in the scanning room and, once the physician and/or the technician initiate the fluid injection procedure on the fluid injector system 100, the image capture device 200 may be used to delay the start of the fluid injection procedure until it has been identified that the physician and/or the technician has left the scanning room.

In some examples of the present disclosure, the image capture device 200 may also be used to ensure that unwanted or unauthorized individuals do not enter the scanning room during a scanning procedure or while a patient is in the scanning room. For example, the image capture device 200 may be configured to capture image data and/or video data of the scanning room during a scanning or fluid injection procedure. In the event an individual walks into the scanning room during this procedure, the image capture device 200 may be configured to capture image data and/or video data of the individual, resulting in the fluid injector system 100 suspending the procedure until the individual leaves or is removed from the scanning room.

In some examples of the present disclosure, the image capture device 200 may also be used to capture image data and/or video data of the patient during a fluid injection procedure or a scanning procedure during which the patient should preferably remain motionless. In the event the image capture device 200 identifies that the patient has moved during the procedure, the fluid injector system 100 may be configured to suspend the procedure until the patient remains motionless. In some examples of the present disclosure, the image capture device 200 may be used to identify whether a patient has been directed to a scanner room or whether the scanner room is empty. Using the image capture device 200 in this manner, improvements in scheduling patient procedures are realized since physicians and technicians can immediately identify in real-time whether a scanner room is occupied by a patient. The image capture device 200 may be used to capture image data and/or video data of the patient during the entire image scanning procedure. In some examples of the present disclosure, the image capture device 200 may also be configured to capture image data and/or video data of the scanner room to determine if/when the room has been decontaminated after an image scanning procedure. In the event the scanner room has not yet been decontaminated, the fluid injector system 100 may be configured to warn an individual of this situation when he/she steps into the contaminated room.

Figure 10:
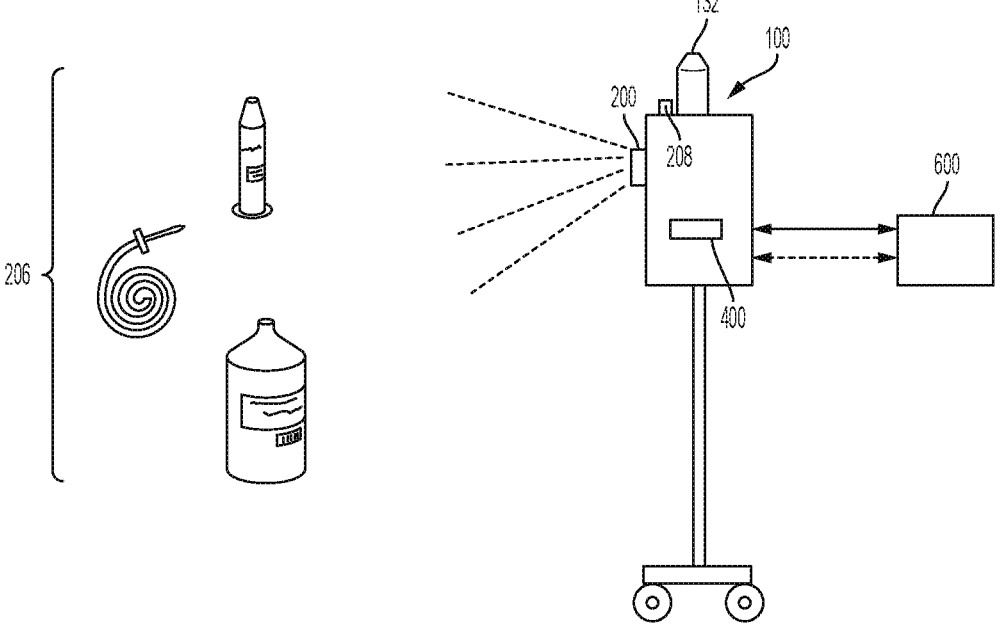
FIG. 10 is a schematic view of a fluid injector system including an image capture device capturing object identification information of an object in accordance with some non-limiting examples of the present disclosure.

With reference to FIG. 10, in some examples of the present disclosure, a further use of the image capture device 200 in conjunction with the fluid injector system 100 is shown and described. Similar to the facial recognition programs identified above, the image capture device 200 may also be used to recognize objects placed in or near the fluid injector system 100. Using the image capture device 200, image data or video data of an object 206 that is placed in front of the image capture device 200 may be captured by the image capture device 200. The image data or the video data of the object 206 may be sent to the electronic control device 400 for evaluation. In some examples of the present disclosure, the image capture device 200 may be configured and programmed to capture image data or video data of the object 206 including a label, a barcode, a shape of the object 206, a color of the object 206, the color of the fluid contained in the object 206, and/or a QR code provided on the object 206. In some examples, the object 206 may be a syringe, a bulk fluid container, or a catheter set, among other items that may be used with the fluid injector system 100. After the image capture device 200 captures the image data or the video data of the object 206 and sends this information to the electronic control device 400, the electronic control device 400 may auto-document the particular object 206 that is being used with the fluid injector system 100 based on the image data or the video data. In some examples, based on the captured label, barcode, and/or QR code, information regarding the object 206 may be identified by the electronic control device 400 such as syringe parameters including volume, dimensions, and material, a particular fluid held in a bulk fluid container, a gauge size and/or length of a catheter set, and a multiple-use disposable syringe set or a single-use disposable syringe set that is inserted into the fluid injector system 100. The auto-documentation of this information regarding the object 206 eliminates the need to manually enter this data into the fluid injector system 100 and ensures accuracy and compliance regarding this information that is entered into the fluid injector system 100. Further, by eliminating the need to manually enter this information regarding the object 206, it permits the physician or technician to spend more time with the patient.

In some examples of the present disclosure, the image data and/or the video data of the object 206 captured by the image capture device 200 may be stored in the electronic control device 400 of the fluid injector system 100 or may be directed to a remote central database 600 for storage for future use. The image data and/or the video data of the object 206 may be captured by the image capture device 200 by placing the object 206 in front of the image capture device 200 or by moving the image capture device 200 in front of the object 206.

In some examples of the present disclosure, the image data and/or the video data of the object 206 may be used by the electronic control device 400 and/or the central database 600 for inventory tracking in a facility. By recording information regarding the object 206 that is being used with the fluid injector system 100, the electronic control device 400 and/or the central database 600 may keep track of the number of objects, such as syringes, catheter sets, and/or bulk fluid containers, that are still stored in the facility for use by other fluid injector systems 100. Once it has been identified that the supply of the particular objects 206 is low, the facility may be alerted that additional objects 206 need to be ordered to replenish the inventory of the facility. The information regarding the object 206 obtained from the image data and/or the video data of the object 206 may be displayed on the user interface 124 of the fluid injector system 100 to inform the physician or the technician using the fluid injector system 100 of the relevant information regarding the object 206. In some examples of the present disclosure, text information for the object 206 identified by the image capture device 200 may be recorded by the electronic control device 400 using the image data and/or the video data so that the text information may be populated into point-of-care fields to be added to an injection record that is recorded for the patient connected to the fluid injector system 100. The patient's injection record may be stored in the electronic control device 400 or the central database 600 for future reference by the physician or the technician. An example of a system into which the central database 600 could be incorporated is the Certegra® Workstation offered by Bayer HealthCare LLC.

In some examples of the present disclosure, the image capture device 200 may capture image data and/or video data of a bulk fluid container or a syringe containing a contrast medium or a diluent such as saline. The image data and/or the video data captured by the image capture device 200 may include the manufacturer of the contrast medium, an expiration date of the contrast medium, a lot or batch number for the contrast medium, and/or a concentration of the contrast medium. All of this information may be reviewed by the physician or the technician to allow him/her to ensure that the contrast medium that is being injected to a patient is safe for injection. In the event an issue arises regarding the particular contrast medium used in the fluid injector system 100, the recorded image data and/or video data can be reviewed to identify particular details regarding the contrast medium, such as the lot or batch number of the contrast medium, to reduce the number of issues that may be experienced by using contrast medium from the same manufacturer and/or lot or batch.

Figure 11:
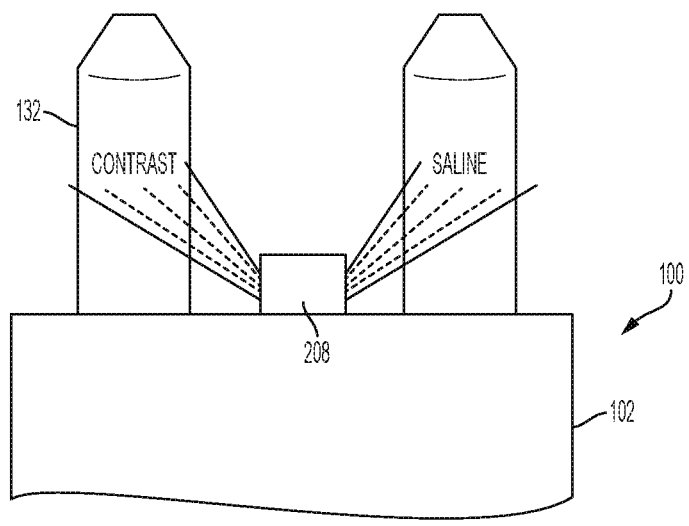
FIG. 11 is a schematic view of a fluid injector system having a projection system in accordance with some non-limiting examples of the present disclosure.

With reference to FIG. 11, in some examples of the present disclosure, a further use of the image capture device 200 in connection with the fluid injector system 100 is shown and described. Once the image capture device 200 has captured the image data and/or the video data regarding the object 206, the electronic control device 400 may use this information to perform additional functions with the fluid injector system 100. In some examples of the present disclosure, the image capture device 200 may be used to identify non-magnetic resonance safe objects that are in the scanner room 15. In this situation, the fluid injector system 100 may be configured to prevent any fluid injection procedures until the non-magnetic resonance safe object is removed from the scanner room 15. In some examples of the present disclosure, the fluid injector system 100 may also include a projection system 208 provided on the injector housing 102. The projection system 208 may be positioned near a syringe 132 that is held in the fluid injector system 100. The projection system 208 may be used to display information on an outer surface of the syringe 132 and/or an inner surface of the syringe 132. In some examples of the present disclosure, the projection system 208 may include at least one light that is configured to illuminate the body of the syringe 132 to display information on the syringe 132. In some examples of the present disclosure, after the image capture device 200 has scanned at least one of the syringes 132, a bulk fluid container, and a catheter set, the electronic control device 400 may be configured and programmed to instruct the projection system 208 to display the information on the body of the syringe 132, including such information as the type of fluid held in the syringe 132, the expiration date of the fluid held in the syringe 132, the manufacturer of the syringe 132 or the fluid held in the syringe 132, the date and/or time that the syringe 132 was installed in the fluid injector system 100, and the volume of fluid remaining in the syringe 132. By displaying this information on the body of the syringe 132, the physician or the technician can constantly identify the information regarding the administered medications to the patient. Further, by displaying this information on the body of the syringe 132, the risk of using the incorrect medication on a patient may be reduced since the physician or the technician is constantly reminded of the information regarding the fluid held in the syringe 132. The displayed information also assists in decreasing the number of manual steps a physician or technician needs to take to identify the particular fluid held in the syringe 132, which leads to increased time with the patient.

In some examples of the present disclosure, the projection system 208 may be used to detect any errors in the fluid that is loaded into the fluid injector system 100. For example, the projection system 208 may be programmed to always display a label on the syringe that identifies the specific type of fluid, including contrast and saline, that should be loaded into each specific syringe 132. Therefore, once a physician or a technician has loaded the syringe(s) 132 into the fluid injector system 100, the projection system 208 will illuminate the desired fluid indicator on the syringe 132 to allow the physician or the technician to review the installed syringe(s) 132 and verify that the correct fluid has been provided in the correct syringe(s) 132 before an injection procedure is initiated for the fluid injector system 100. In the event the physician or the technician identifies that the incorrect fluid is provided in the syringe(s) 132, the physician or the technician will quickly identify this situation and will switch the syringe(s) 132. The electronic control device 400 may also store preprogrammed tasks that are to be performed by the fluid injector system 100. Based on the selected task, the electronic control device 400 will instruct the projection system 208 to display the appropriate syringe indicators on the body of the syringe 132. In some examples of the present disclosure, the image capture device 200 may also be configured and programmed to identify the type of fluid held in the syringe(s) 132 and will either permit operation of the fluid injector system 100 in the event the correct fluid is held in the syringe(s) 132 or will lock the fluid injector system 100 from operation until the correct fluid is introduced into the syringe(s) 132. The image capture device 200 may identify the fluid held in the syringe(s) 132 based on the color, the density, or other characteristics of the fluid. In some examples of the present disclosure, in the event the image capture device 200 identifies that the syringe(s) 132 have been incorrectly installed in the fluid injector system 100, the fluid injector system 100 may be configured to issue a visual and/or audio alert to the physician or the technician and may lock the wheels of the base 110 of the fluid injector system 100.

Figure 12:
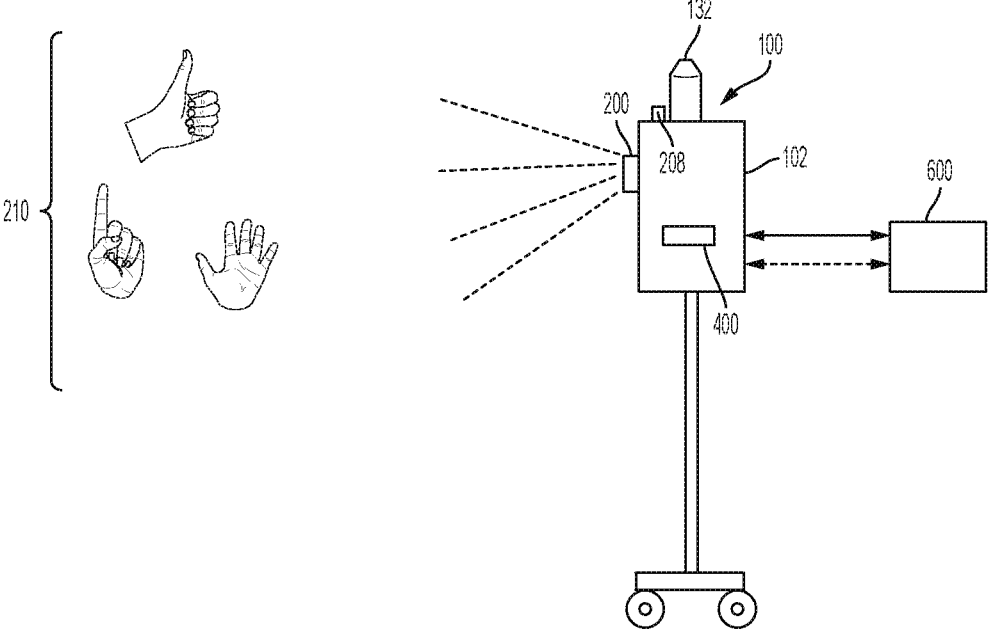
FIG. 12 is a schematic view of a fluid injector system including an image capture device capturing hand gesture information of an individual in accordance with some non-limiting examples of the present disclosure.

With reference to FIG. 12, in some examples of the present disclosure, a further operation and method of use of the image capture device 200 and the fluid injector system 100 is shown and described. Similar to the facial recognition operation described in connection with FIG. 9, a hand gesture recognition operation may be initiated by the fluid injector system 100 to perform certain preprogrammed tasks based on the specific hand gesture 210 performed by a physician or a technician that is captured by the image capture device 200. By using the hand gesture recognition operation with the fluid injector system 100, sterility techniques provided for the fluid injector system 100 are improved since the physician or the technician does not need to touch the fluid injector system 100 in order to instruct the fluid injector system 100 to perform certain tasks. Furthermore, information recordation for a patient may be improved by storing the recorded hand gestures as video data with a particular patient file. By using a hand gesture recognition operation with the fluid injector system 100, the wear and tear of the buttons and the user interface 124 of the fluid injector system 100 is also reduced since the physician or the technician does not need to touch the buttons or the user interface 124 as often.

In some examples of the present disclosure, the image capture device 200 may be configured to capture image data and/or video data regarding a hand gesture 210 performed by an individual positioned near the fluid injector system 100. For example, the image capture device 200 may be configured to take a photograph or video of a hand gesture 210 performed by a physician or a technician that is positioned near the fluid injector system 100. The image data and/or the video data captured by the image capture device 200 may include hand gesture identification information regarding the hand gesture 210 performed by the individual that is sent to the electronic control device 400 of the fluid injector system 100 via a wired or a wireless communication. Once the electronic control device 400 receives the hand gesture identification information, the electronic control device 400 may be configured and programmed to compare the captured hand gesture identification information to hand gesture identification information stored either in the electronic control device 400 or a central database 600 in communication with the electronic control device 400.

In some examples of the present disclosure, upon receiving a positive match between the captured hand gesture identification information captured by the image capture device 200 and the stored hand gesture identification information, the fluid injector system 100 may be activated to perform a predetermined operation or task based on the captured hand gesture identification information. In some examples of the present disclosure, after a preprogrammed task has been selected by the physician or the technician using the user interface 124 of the fluid injector system 100 and the physician or the technician has verified that the patient has been properly prepared for the task, the physician or the technician may perform a "thumbs-up" hand gesture 210 in front of the image capture device 200 to authorize the fluid injector system 100 to perform the selected predetermined operation or task. In some examples of the present disclosure, during a preprogrammed task or operation that is being performed by the fluid injector system 100, the physician or the technician may perform a "stop" hand gesture 210 in front of the image capture device 200 to authorize the fluid injector system 100 to stop performing the preprogrammed task or operation. In some examples of the present disclosure, after a preprogrammed task has been selected by the physician or the technician using the user interface 124 of the fluid injector system 100 and the physician or the technician has verified that the patient has been properly prepared for the task, the physician or the technician may perform a hand gesture 210 in front of the image capture device 200 that holds up a number of fingers that may correspond to the number of minutes the fluid injector system 100 should wait until the selected preprogrammed task or operation is initiated by the fluid injector system 100.

In some examples of the present disclosure, the image capture device 200 may also be programmed to capture image data and/or video data of user actions that are performed to operate the fluid injector system 100. The captured user actions may be used to support remote learning and training for the fluid injector system 100. The image capture device 200 may be positioned to observe the user or operator interaction with the fluid injector system 100 keyboard, console, user interface 124, and/or any other user interface elements or components of the fluid injector system 100. After this image data and/or video data has been sent to the electronic control device 400, the electronic control device 400 may be programmed to provide information regarding specific user actions that could be used in the future to provide cues to assist the user or operator or to inform training personnel so that he/she can provide feedback to a trainee or better understand areas to focus on for user training. To relieve concerns about patient and/or operator privacy, the image capture device 200 could electronically "blur" the operator and patient facial features and only focus on hands and arms of the patient and/or operator and their associated motions and gestures.

In some examples of the present disclosure, the fluid injector system 100 may be programmed to permit a physician or a technician to select a preprogrammed task or operation and then to set his/her own preprogrammed hand gesture 210 with the fluid injector system 100 to program the fluid injector system 100 to initiate the selected preprogrammed task or operation upon identifying the preprogrammed hand gesture 210 from the physician or the technician. In some examples of the present disclosure, the fluid injector system 100 may instruct the physician or the technician to perform a certain task, such as confirming that no air is visibly present in a catheter set, before the fluid injector system 100 will perform a preprogrammed task. After completing the task identified by the fluid injector system 100, the physician or the technician may conduct a "thumbs-up" hand gesture 210 in front of the image capture device 200 to confirm that the task has been completed and the fluid injector system 100 is permitted to begin the preprogrammed task or operation. In some examples of the present disclosure, the image capture device 200 may also capture image data or video data of the physician or the technician performing and completing the task for future review in the event an adverse or undesired event occurs with the fluid injector system 100. In some examples of the present disclosure, the image capture device 200 may be used to identify whether or not the physician or technician has completed the air check before initiating the procedure. In the event the air check has not been completed by the physician or the technician, the fluid injector system 100 will not initiate the fluid injection procedure. In some examples of the present disclosure, the hand gestures 210 recognized by the fluid injector system 100 may be cultural-specific gestures that adapt to a particular region or location in which the fluid injector system 100 is being used. In some examples of the present disclosure, the hand gestures 210 recognized by the fluid injector system 100 may include a zoom-in gesture, a zoom-out gesture, and a swiping gesture to instruct the fluid injector system 100 to perform a certain preprogrammed procedure.

In some examples of the present disclosure, the image capture device 200 may also be configured and programmed to capture image data and/or video data of a physician's or technician's hand as he/she performs an intravenous needle injection procedure. The image capture device 200 may capture the image data and/or video data of the particular injection flow rate, the type of fluid, and/or the injection timing performed by the physician or the technician.

Figure 13:
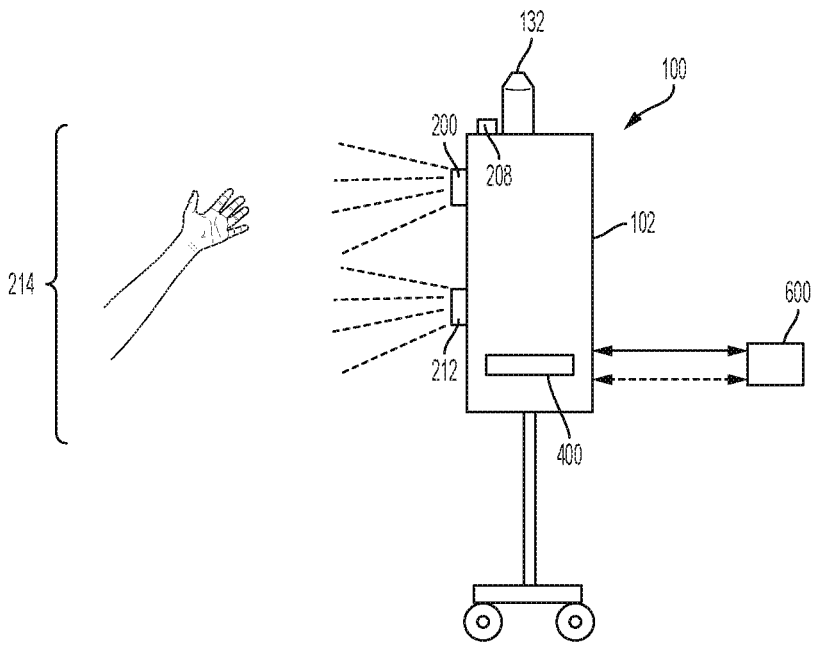
FIG. 13 is a schematic view of a fluid injector system including an image capture device and a near-infrared projection system for vein mapping of a patient in accordance with some non-limiting examples of the present disclosure.

With reference to FIG. 13, in some examples of the present disclosure, a further operation and method of use of the image capture device 200 and the fluid injector system 100 is shown and described. In some examples of the present disclosure, the fluid injector system 100 may also include a near-infrared projection system 212 that may be utilized to map a patient's veins. Once the patient has been positioned near the fluid injector system 100, a patient's limb 214 may be positioned in front of the fluid injector system 100 so the near-infrared projection system 212 can map the patient's veins for easy identification by the physician or the technician. By using this vein mapping, the physician or the technician is provided an accurate visualization of the patient's veins underneath his/her skin. Once the near-infrared projection system 212 detects the patient's veins using an infrared light, the near-infrared projection system 212 digitally displays the patient's vein mapping on the surface of the patient's skin so the physician or the technician can easily visualize and identify veins in the patient's limb 214 for insertion of an intravenous needle. The near-infrared projection system 212 may be formed integral with the injector housing 102 of the fluid injector system 100. In another example of the present disclosure, the near-infrared projection system 212 may be operatively connected to the fluid injector system 100 via an extension member that allows the physician or the technician to move the near-infrared projection system 212 relative to the fluid injector system 100 to accommodate different positions for the patient relative to the fluid injector system 100.

In some examples of the present disclosure, after the near-infrared projection system 212 has mapped the patient's veins on the surface of the patient's skin, the image capture device 200 may capture image data and/or video data of the vein mapping for recordation on the electronic control device 400 or in the central database 600. The image data and/or the video data captured by the image capture device 200 may be displayed on the user interface 124 of the fluid injector system 100 to help the physician or the technician easily identify the patient's vein mapping. By visualizing the patient's vein mapping, the physician or the technician can improve his/her intravenous needle placement efforts to enhance the safety and efficiency of inserting an intravenous needle into an appropriate vessel in the patient's limb 214. In some examples of the present disclosure, the image capture device 200 may capture image data and/or video data of the specific insertion location of the intravenous needle in the patient's limb 214 and may be recorded using the electronic control device 400 and/or the central database 600 for future reference. In some examples of the present disclosure, the image capture device 200 may detect the intravenous needle being inserted into the patient's limb 214 and will document a verification in the electronic control device 400 and/or the central database 600 to create a record that the intravenous needle was inserted into the patient. By using the vein mapping in tandem with the image capture device 200, extravasation in the patient can be avoided. Further, less time working on challenging intravenous needle placement may be afforded by using the image capture device 200 in tandem with the vein mapping, which leads to increased patient throughput and allow for more time for other workflow steps for the physician or the technician.

In some examples of the present disclosure, the near-infrared projection system 212 may also be used to display an illuminated pattern on the patient's limb 214. In some examples, the pattern may be a checkered pattern or a plurality of parallel lines. After the pattern has been illuminated on the patient's limb 214, the image capture device 200 may be configured and programmed to capture image data and/or video data of the pattern on the patient's limb 214 to detect any dimensional changes in the pattern that are created due to swelling of the patient's limb 214. The electronic control device 400 may review and calculate these dimensional changes in the pattern to determine the full extent of swelling in the patient's limb 214.

In some examples of the present disclosure, a further operation and method of use of the image capture device 200 and the fluid injector system 100 is described. In some examples of the present disclosure, the image capture device 200 may be configured to capture image data and/or video data of an environment near the fluid injector system 100 to automatically detect adverse or undesired events that may occur when treating a patient. In some examples of the present disclosure, an adverse or undesired event may be any event that adversely affects a patient that is connected to the fluid injector system, including incorrect intravenous needle insertion placement, incorrect fluid type injection, incorrect fluid flow rate utilized by the fluid injector system 100, allergic reactions in the patient, extravasation, and inadvertent removal of an intravenous needle in the patient's limb. In some examples of the present disclosure, an adverse or undesired event may include patient distress before, during, and/or after an injection procedure, including an allergic reaction, an accelerated heart rate for the patient or movement from the patient, hypoxia, and incorrect container connections within the fluid injector system 100. By using the image capture device 200 to detect the adverse event, the time of recognition of the adverse or undesired event may be improved and an image and/or video may be captured by the image capture device 200 for quality assurance purposes and for safety initiatives that are taught to physicians and technicians when learning to use the fluid injector system 100. In some examples, the electronic control device 400 of the fluid injector system 100 may be programmed and configured to use a high-powered video magnification algorithm to detect changes in blood flow in the patient using the image data and/or video data captured by the image capture device 200. In some examples of the present disclosure, in the event the image capture device 200 and the electronic control device 400 detect an adverse or undesired event with the patient, the image capture device 200 may be programmed to automatically capture an image or record a video of the patient during the adverse or undesired event. In some examples of the present disclosure, after the image or video has been captured, the electronic control device 400 and/or the central database 600 may archive the image or video for future review and artificial intelligence learning for the fluid injector system 100. The fluid injector system 100 may be programmed to review these archived images and/or videos to identify early indicators for adverse or undesired events that may be detected before the adverse or undesired event occurs to allow the fluid injector system 100 to adjust before the adverse or undesired event occurs. In some examples of the present disclosure, image data and/or video data may be captured by the image capture device 200 of the intravenous needle insertion into the patient's vessel and delivery of medical fluid to the patient for associated adverse or undesired event reporting and documentation in the event an adverse or undesired event occurs during an injection procedure for the fluid injector system 100.

While various examples of the present disclosure were provided in the foregoing description, those skilled in the art may make modifications and alterations to these examples without departing from the scope and spirit of the disclosure. Accordingly, the foregoing description is intended to be illustrative rather than restrictive. The disclosure described hereinabove is defined by the appended claims, and all changes to the disclosure that fall within the meaning and the range of equivalency of the claims are to be embraced within their scope.

We claim:

1. A fluid injector system configured for use in administering at least one fluid to a patient, the fluid injector system comprising:

at least one image capture device configured for capturing image data or video data in an environment surrounding the fluid injector system; and a control device comprising at least one processor programmed or configured to:

receive, with the at least one processor, the image data or the video data captured by the at least one image capture device;

determine, with the at least one processor, whether the received image data or the received video data comprises at least one predetermined characteristic; and perform, with the at least one processor, at least one action in response to determining whether the received image data or the received video data comprises at least one predetermined characteristic, wherein the control device is configured to:

receive, from the at least one image capture device, facial identification information or biometric information regarding a user based on an image or a video of the user positioned near the fluid injector system and an image or a video of a fluid container positioned near the fluid injector system, compare the received facial identification or biometric identification information regarding the user to a stored facial identification information or biometric identification information to determine whether the user is an individual authorized to use the fluid injector system, and display the received image or video of the fluid container on the preferred user interface, wherein the control device is configured to set the fluid injector system to a preferred user interface upon receiving a confirmed match between the received facial identification information or the biometric identification information and the stored facial identification information or the biometric identification information, in which the preferred user interface is a user interface configuration that has been previously set on the fluid injector system corresponding to a specific user.

2. The fluid injector system of claim 1, wherein the at least one image capture device is at least one camera, the at least one camera being at least one of: a) integrally formed with an injector housing of the fluid injector system, and b) operatively connected to an injector housing of the fluid injector system via an extendable member that permits the at least one camera to be moved relative to the injector housing.

3. The fluid injector system of claim 1, wherein the control device is configured to:

receive, from the at least one image capture device, facial identification information or biometric identification information regarding a patient based on an image or a video of the patient positioned near the fluid injector system, and retrieve patient records for the patient based on the facial identification information or the biometric identification information received by the control device regarding the patient.

4. The fluid injector system of claim 1, wherein the at least one image capture device is configured to capture at least one image of at least one of a label on an object, a barcode on the object, a color of the object, a color of a fluid contained in the object, a shape of the object, and a QR code of the object positioned near an injector housing of the fluid injector system.

5. The fluid injector system of claim 4, wherein the control device is configured to automatically document details regarding the object based on the shape, the color, the label, the barcode, or the QR code captured by the at least one image capture device.

6. The fluid injector system of claim 4, wherein the control device is configured to forward information regarding the object identified by the at least one image capture device to a central database to assist in inventory tracking of the object.

7. The fluid injector system of claim 4, further comprising a projection system provided on the injector housing of the fluid injector system, wherein the projection system is configured to display information on at least one syringe held in the fluid injector system corresponding to the object identified by the at least one image capture device.

8. The fluid injector system of claim 1, wherein the at least one image capture device is configured to capture an image or a video of at least one hand gesture performed by an individual positioned near the fluid injector system, wherein the control device is configured to receive hand gesture identification information from the at least one image capture device based on the at least one hand gesture performed by the individual, and wherein the control device is configured to conduct a predetermined operation based on the hand gesture identification information received from the at least one image capture device.

9. The fluid injector system of claim 1, further comprising a near-infrared projection system that is configured to perform at least one of: a) vein mapping on a patient positioned near the fluid injector system, wherein the at least one image capture device is configured to capture at least one image or video of the vein mapping of the patient, and b) a pattern illumination on a limb of the patient, wherein the at least one image capture device is configured to capture at least one image or video of the pattern illuminated on the patient's limb.

10. The fluid injector system of claim 1, wherein the at least one image capture device is positioned and configured to capture at least one image or video of at least one of: a) an insertion site of an intravenous needle on a patient positioned near the fluid injector system, and b) a patient positioned near the fluid injector system to detect a change in blood flow of the patient.

11. The fluid injector system of claim 10, wherein the control device is configured to record the at least one image or video in a central database for future review upon an adverse event occurring in connection with use of the fluid injector system.

12. A computer-implemented method for operating a fluid injector system configured for use in administering at least one fluid to a patient, the method comprising:

capturing, with at least one image capture device, facial identification information or biometric information regarding a user in an environment surrounding the fluid injector system and an image or a video of a fluid container positioned near the fluid injector system;

receiving, with a control device comprising at least one processor, the image data or the video data captured by the at least one image capture device regarding the user and the fluid container;

comparing the received facial identification or biometric identification information regarding the user to a stored facial identification information or biometric identification information to determine whether the user is an individual authorized to use the fluid injector system;

setting the fluid injector system to a preferred user interface upon receiving a confirmed match between the received facial identification information or the biometric identification information and the stored facial identification information or the biometric identification information, in which the preferred user interface is a user interface configuration that has been previously set on the fluid injector system corresponding to a specific user, and displaying the received image or video of the fluid container on the preferred user interface.

13. A computer program product for operating a fluid injector system configured for use in administering at least one fluid to a patient, the computer program product comprising at least one non-transitory computer-readable medium comprising one or more instructions that, when executed by at least one processor, cause the at least one processor to:

capture, with at least one image capture device, image data or video data in an environment surrounding the fluid injector system, wherein the at least one image capture device is at least one of: a) integrally formed with an injector housing of the fluid injector system, and b) operatively connected to an injector housing of the fluid injector system via an extendable member that permits the at least one image capture device to be moved relative to the injector housing;

receive the image data or the video data captured by the at least one image capture device;

determine whether the received image data or the received video data comprises at least one predetermined characteristic; and perform at least one action in response to determining whether the received image data or the received video data comprises at least one predetermined characteristic;

wherein the one or more instructions further cause the at least one processor to:

receive, with a control device of the fluid injector system and from the at least one image capture device, facial identification information or biometric identification information regarding a user based on an image or a video of the user positioned near the fluid injector system and image or video data regarding a fluid container positioned near the fluid injector system, compare, using the control device, the received facial identification information or biometric identification information regarding the user to a stored facial identification information or biometric identification information to determine whether the user is an individual authorized to use the fluid injector system, upon receiving a confirmed match between the received facial identification information or biometric identification information and the stored facial identification information or biometric identification information, set the fluid injector system to a preferred user interface in which the preferred user interface is a user interface configuration that has been previously set on the fluid injector system corresponding to a specific user, and display the received image or video data of the fluid container on the preferred user interface.

14. The computer program product of claim 13, wherein the one or more instructions further cause the at least one processor to:

receive, using the control device and from the at least one image capture device, facial identification information or biometric identification information regarding a patient based on an image or a video of the patient positioned near the fluid injector system, and retrieve, using the control device, patient records for the patient based on the facial identification information or biometric identification information received by the control device regarding the patient.

15. The computer program product of claim 13, wherein the one or more instructions further cause the at least one processor to:

capture, with the at least one image capture device, at least one image of at least one of a label on an object, a barcode on the object, a color of the object, a color of a fluid contained in the object, a shape of the object, and a QR code of the object positioned near an injector housing of the fluid injector system;

automatically document, using the control device, details regarding the object based on the shape, the color, the label, the barcode, or the QR code captured by the at least one image capture device; and forward, using the control device, information regarding the object identified by the at least one image capture device to a central database to assist in inventory tracking of the object.

16. The computer program product of claim 13, wherein the fluid injector system further comprises a projection system provided on the injector housing of the fluid injector system, and wherein the one or more instructions further cause the at least one processor to display, using the projection system, information on at least one syringe held in the fluid injector system corresponding to the object identified by the at least one image capture device.

17. The computer program product of claim 13, wherein the one or more instructions further cause the at least one processor to:

capture, using the at least one image capture device, an image or a video of at least one hand gesture performed by an individual positioned near the fluid injector system, receive, using the control device, hand gesture identification information from the at least one image capture device based on the at least one hand gesture performed by the individual, and conduct, using the control device, a predetermined operation based on the hand gesture identification information received from the at least one image capture device.

18. The computer program product of claim 13, wherein the fluid injector system further comprises a near-infrared projection system that is configured to perform at least one of: a) vein mapping on a patient positioned near the fluid injector system, wherein the one or more instructions further cause the at least one processor to capture, using the at least one image capture device, at least one image or video of the vein mapping of the patient, and b) pattern illumination on a limb of the patient, wherein one or more instructions further cause the at least one processor to capture, using the at least one image capture device, at least one image or video of the pattern illuminated on the patient's limb.

19. The computer program product of any of claim 13, wherein the one or more instructions further cause the at least one processor to configure the at least one image capture device to capture at least one image or video of at least one of: a) an insertion site of an intravenous needle on a patient positioned near the fluid injector system, and b) a patient positioned near the fluid injector system to detect a change in blood flow of the patient.

20. The computer program product of claim 13, wherein the one or more instructions further cause the at least one processor to record, using the control device, the image data in a central database for future review upon an adverse event occurring in connection with use of the fluid injector system.

\*  \*  \*  \*  \*